United States Patent
Moody et al.

(10) Patent No.: US 11,091,752 B2
(45) Date of Patent: Aug. 17, 2021

(54) SQUALENE HOPENE CYCLASE AND USE THEREOF FOR PRODUCING AMBROXAN

(71) Applicant: INTERNATIONAL FLAVORS & FRAGRANCES INC., New York, NY (US)

(72) Inventors: Thomas Shaw Moody, Ballymena (IE); Iain Robert Miskelly, Tandragee (GB); Derek John Quinn, Newtownards (GB)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

(21) Appl. No.: 16/487,196

(22) PCT Filed: Feb. 26, 2018

(86) PCT No.: PCT/US2018/019633
§ 371 (c)(1),
(2) Date: Aug. 20, 2019

(87) PCT Pub. No.: WO2018/157021
PCT Pub. Date: Aug. 30, 2018

(65) Prior Publication Data
US 2020/0385700 A1    Dec. 10, 2020

Related U.S. Application Data

(60) Provisional application No. 62/463,163, filed on Feb. 24, 2017.

(51) Int. Cl.
*C12P 17/04*    (2006.01)
*C12N 9/90*    (2006.01)

(52) U.S. Cl.
CPC .............. *C12N 9/90* (2013.01); *C12P 17/04* (2013.01); *C12Y 504/99017* (2013.01)

(58) Field of Classification Search
None
See application file for complete search history.

(56) References Cited

U.S. PATENT DOCUMENTS

2020/0385700 A1* 12/2020 Moody ................... C12P 17/04

FOREIGN PATENT DOCUMENTS

WO    2016170099 A1    10/2016

OTHER PUBLICATIONS

Dang et al. (2000) "Site-directed mutagenesis of squalene-hopene cyclase: altered substrate specificity and product distribution." Chem. Biol. 7(8):643-9.
Hoshino et al., Squalene-hopene cyclase [Gluconobacter morbifer], Genbank Accession No. WP_040507485, Jun. 19, 2019.
International Preliminary Report on Patentability in PCT/US2018/019633 dated Aug. 27, 2019.
International Search Report and Written Opinion in PCT/US2018/019633 dated Jul. 9, 2018.
Lee et al., Squalene-hopene cyclase [Gluconobacter morbifer G707], Genbank Accession No. EHH-169691, Nov. 4, 2011.
Lenhart, et al. (2002) "Crystal Structure of a Squalene Cyclase in Complex with the Potential Anticholesteremic Drug Ro48-8071." Chem. Biol. 9:639-45.
UNIPROTKB entry G6XHN3, Squalene-hopene cyclase, Jan. 25, 2012.

* cited by examiner

*Primary Examiner* — Hope A Robinson
(74) *Attorney, Agent, or Firm* — Licata & Tyrrell P.C.

(57) ABSTRACT

A Squalene Hopene Cyclase (SHC) isolated from *Gluconobacter morbifer* is provided as are variants and a method for using the *G. morbifer* SHC to biocatalytically convert homofarnesol to ambroxan.

6 Claims, 4 Drawing Sheets

Specification includes a Sequence Listing.

```
GmSHC    ------------------------------------------MSPADISTKSSS--FQR
ZmSHC    MGIDRMNSLSRLLMKKIFGAEKTSYKPASDTIIGTDTLKRPNRRPEPTAKVDKTI--FKT
BspSHC   ---------------------------------------MTVTSSASARATRDPGN
RpSHC    ------------------------------------------MDSILAPRADA---PRN
ScSHC    ------------------------------------------MTATTDGSTGAS--LRP
BamSHC   ------------------------------------------------------MND
BanSHC   ------------------------------------------------------------
AaSCH    ------------------------------------------------------------

GmSHC    LDN-----------------MLPEAVSSACDWLIDQQKPDGHWVGPVESNACMEAQWC
ZmSHC    MGN-----------------SLNNTLVSACDWLIGQQKPDGHWVGAVESNASMEAEWC
BspSHC   YQT-----------------ALQSTVRAAADWLIANQKPDGHWVGRAESNACMEAQWC
RpSHC    IDG-----------------ALRESVQQAADWLVANQKPDGHWVGRAETNATMEAQWC
ScSHC    LAASASDTDITIPAAAAG-VPEAAARATRRATDFLLAKQDAEGWWKGDLETNVTMDAEDL
BamSHC   LTE--------MATLSAGTVPAGLDAAVASATDALLAAQNADGHWVYELEADSTIPAEYV
BanSHC   MSN-LLLYE-----------KAHEEIVRRATALQTMQWQDGTWRFCFEGAPLTDCHMI
AaSCH    ----------MAEQLVE-AP-AYARTLDRAVEYLLSCQKDEGYWWGPLLSNVTMEAEYV

GmSHC    LALWFLGQEDH-PLRPRLAQALLEMQREDGSWGIYVGADHGDINTTVEAYAAL-RSMGYA
ZmSHC    LALWFLGLEDH-PLRPRLGNALLEMQREDGSWGVYFGAGNGDINATVEAYAAL-RSLGYS
BspSHC   LALWFMGLEDH-PLRKRLGQSLLDSQRPDGAWQVYFGAPNGDINATVEAYAAL-RSLGFR
RpSHC    LALWFLGLEDH-PLRVRLGRALLDTQRPDGAWHVFYGAPNGDINATVEAYAAL-RSLGHR
ScSHC    LLRQFLGIQDE-ETTRAAALFIRGEQREDGTWATFYGGP-GELSTTIEAYVAL-RLAGDS
BamSHC   LLVHYLGETPNLELEQKIGRYLRRVQQADGGWPLFTDGA-PNISASVKAYFAL-KVIGDD
BanSHC   FLLKLLGRDKE---IEPFVERVASLQTNEGTWKLHEDEVGGNLSATIQSYAALLASKKYT
AaSCH    LLCHILDRVDR-DRMEKIRRYLLHEQREDGTWALYPGGP-PDLDTTIEAYVAL-KYIGMS

GmSHC    ADMPIMAKSAAWIQQKGGLRNVRVFTRYWLALIGEWPWDKTPNLPPEIIWLPDNFIFSIY
ZmSHC    ADNPVLKKAAAWIAEKGGLKNIRVFTRYWLALIGEWPWEKTPNLPPEIIWFPDNFVFSIY
BspSHC   DDEPAVRRAREWIEAKGGLRNIRVFTRYWLALIGEWPWEKTPNIPPEVIWFPLWFPFSIY
RpSHC    DDEEPLRKARDWILSKGGLANIRVFTRYWLALIGEWPWEKTPNILPEVIWLPTWFPFSIY
ScSHC    PEAPHMARAAEWIRSRGGIASARVFTRIWLALFGWWKWDDLPELPPELIYFPTWVPLNIY
BamSHC   ENAEHMQRARRAIQAMGGAEMSNVFTRIQLALYGAIPWRAVPMMPVEIMLLPQWFPFHLS
BanSHC   KEDANMKRAENFIQERGGVARAHFMTKFLLAIHGEYEYPSLFHLPTPIMFLQNDSPFSIF
AaSCH    RDEEPMQKALRFIQSQGGIESSRVFTRMWLALVGEYPWEKVPMVPPEIMFLGKRMPLNIY

GmSHC    NFAQWARATMMPLTILSARRPSRPLLPENRLDGLFPEGRE-NFDYELPVKGEEDLW----
ZmSHC    NFAQWARATMVPIAILSARRPSRPLRPQDRLDELFPEGRA-RFDYELPKKEGIDLW----
BspSHC   NFAQWARATLMPIAVLSARRPSRPLPPENRLDALFPHGRK-AFDYELPVKAGAGGW----
RpSHC    NFAQWARATLMPIAVLSAHRPSRPLAPQDRLDALFPQGRD-SFNYDLPARLGAGVW----
ScSHC    DFGCWARQTIVPLTIVSAKRPVRPAP--FPLDELHTDP---ARPNPPRLAPVASW----
BamSHC   KVSYWARTVIVPLLVLNAKRPIAKNPRGVRIDELFVDPPV-NAGLLPRQGHQSPGW----
BanSHC   ELSSSARIHLIPMMLCLNKR--------------FRVGKK-LLPNLNHIAGGGGEWFRED
AaSCH    EFGSWARATVVALSIVMSRQPV------FPLPERARVPELYETDVPPRRRGAKGGG----
```

*FIG. 1A*

```
GmSHC    -GRFFRAADKGLHSLQSFPVRRF---VPREAAIRHVIEWIIRHQDADGGWGGIQPPWIYG
ZmSHC    -SQFFRTTDRGLHWVQSNLLKRN---SLREAAIRHVLEWIIRHQDADGGWGGIQPPWVYG
BspSHC   -DRFFRGADKVLHKLQNLGNRLN-LGLFRPAATSRVLEWMIRHQDFDGAWGGIQPPWIYG
RpSHC    -DVIFRKIDTILHRLQDWGARRGPHGIMRRGAIDHVLQWIIRHQDYDGSWGGIQPPWIYG
ScSHC    -DGAFQRIDKALHAYRKVAPRRL-----RRAAMNSAARWIIERQENDGCWGGIQPPAVYS
BamSHC   -FAFFRVVDHALRAADGLFPNYT-----RERAIRQAVSFVDERLNGEDGLGAIYPAMANA
BanSHC    RSPVFQTLLSDVKQIISYPLSLH------HKGYEEIERFMKERIDENGTLYSYATASFYM
AaSCH    -GWIFDALDRALHGYQKLSVHPF-----RRAAEIRALDWLLERQAGDGSWGGIQPPWFYA

GmSHC    LMALSVEGYPLHHPVLAKAMDALNDPGWRRDKGDASWI-QATNSPVWDTMLAVLALHDAG
ZmSHC    LMALHGEGYQLYHPVMAKALSALDDPGWRHDRGESSWI-QATNSPVWDTMLALMALKDAK
BspSHC   LMALYAEGYPLNHPVLAKGLDALNDPGWRDVGDATYI-QATNSPVWDTILTLLAFDDAG
RpSHC    LMALHTEGYAMTHPVMAKALDALNEPGWRIDIGDATFI-QATNSPVWDTMLSLLAFDDAG
ScSHC    VIALYLLGYDLEHPVMRAGLESLDR--FAVWREDGARMIEACQSPVWDTCLATIALADAG
BamSHC   VMMYDVLGYAEDHPNRAIARKSIEK--LLVVQEDEAYC-QPCLSPVWDTSLAAHALLETG
BanSHC   IYALLALGHSLQSSMIQKAIAGITSYIWKMERGNHL---QNSPSTVWDTALLSYALQEAQ
AaSCH    LIALKILDMT-QHPAFIKGWEGLEL--YGVELDYGGWMFQASISPVWDTGLAVLALRAAG

GmSHC    AEDRYSPQMDKAIGWLLDRQVR-VKGDWSIKLPDTEPGGWAFEYANDKYPDTDDTAVALI
ZmSHC    AEDRFTPEMDKAADWLLARQVK-VKGDWSIKLPDVEPGGWAFEYANDRYPDTDDTAVALI
BspSHC   VLGDYPEAVDKAVDWVLQRQVR-VPGDWSMKLPHVKPGGWAFEYANNYYPDTDDTAVALI
RpSHC    LGERYPEQVERAVRWVLKRQVL-VPGDWSVKLPDVKPGGWAFEYANNFYPDTDDTSVALM
ScSHC    VPEDH-PQLVKASDWMLGEQIV-RPGDWSVKRPGLPPGGWAFEFHNDNYPDIDDTAEVVL
BamSHC   DARAE-EAVIRGLEWLRPLQILDVRGDWISRRPHVRPGGWAFQYANPHYPDVDDTAVVAV
BanSHC   VSKDN-KMIQNATAYLLKKQHT-KKADWSVHAPALTPGGWGFSDVNTTIPDIDDTTAVLR
AaSCH    LPADH-DRLVKAGEWLLDRQIT-VPGDWAVKRPNLKPGGFAFQFDNVYYPDVDDTAVVVW

GmSHC    ALAGC-RHRPEWRERDIEGAISRGVNWLLAMQSSSGGWGAFDKDNNRSILTKIPFCDFGE
ZmSHC    ALSSY-RDKEEWQKKGVEDAITRGVNWLIAMQSECGGWGAFDKDNNRSILSKIPFCDFGE
BspSHC   ALAPL-RHDPKWKAKGIDEAIQLGVDWLIGMQSQGGGWGAFDKDNNQKILTKIPFCDYGE
RpSHC    ALAPF-RHDPKWQAEGIEDAIQRGIDWLVAMQCKEGGWGAFDKDNDKKILAKIPFCDFGE
ScSHC    ALRRV-RHH---DPERVEKAIGRGVRWNLGMQSKNGAWGAFDVDNTSAFPNRLPFCDFGE
BamSHC   AMDRVQKLK---HNDAFRDSIARAREWVVGMQSSDGGWGAFEPENTQYYLNNIPFSDHGA
BanSHC   ALARS-R-----GNKNIDNAWKKGGNWIKGLQNNDGGWGAFEKGVTSKLLAKLPIENASD
AaSCH    ALNTL-RLP---DERRRRDAMTKGFRWIVGMQSSNGGWGAYDVDNTSDLPNHIPFCDFGE

GmSHC    AL-DPPSVDVTAHVLEAFGLLG---ISRNHPSVQKALAYIRSEQERNGAWFGRWGVNYVY
ZmSHC    SI-DPPSVDVTAHVLEAFGTLG---LSRDMPVIQKAIDYVRSEQEAEGAWFGRWGVNYIY
BspSHC   AL-DPPSVDVTAHIIEAFGKLG---ISRNHPSMVQALDYIRREQEPSGPWFGRWGVNYVY
RpSHC    AL-DPPSADVTAHIIEAFAKVG---LDRNHPSIVRALDYLKREQEPEGPWFGRWGVNYVY
ScSHC    VI-DPPSADVTAHVVEMLAVEG---LAHDPRT-RRGIQWLLDAQETDGSWFGRWGVNYVY
BamSHC   LL-DPPTADVSGRCLSMLAQLGETPLNSEPA--RRALDYMLKEQEPDGSWYGRWGMNYVY
BanSHC   MITDPSTPDITGRVLEFFGTYA-Q-NELPEKQIQRAINWLMNVQEENGSWYGKWGICYLY
AaSCH    VT-DPPSEDVTAHVLECFGSFG---YDDAWKVIRRAVEYLKREQKPDGSWFGRWGVNYLY
```

*FIG. 1B*

```
GmSHC    GTGAVLPALAAIGEDMTQPYIVRACDWLMSVQQENGGWGESCASYMD-INAVG--HGVAT
ZmSHC    GTGAVLPALAAIGEDMTQPYITKACDWLVAHQQEDGGWGESCSSYME-IDSIG--KGPTT
BspSHC   GTGAVLPALAAIGEDMTQPYIGRACDWLVAHQQADGGWGESCASYMD-VSAVG--RGTTT
RpSHC    GTGAVLPALAAIGEDMRQPYIARACDWLIARQQANGGWGESCVSYMD-AKQAG--EGTAT
ScSHC    GTGSVIPALTAAGLPTSHPAIRRAVRWLESVQNEDGGWGEDLRSYRYVREWSG--RGAST
BamSHC   GTWTALCALNAAGLTPDDPRVKRGAQWLLSIQNKDGGWGEDGDSYKL--NYRGFEQAPST
BanSHC   GTWAVMTGLRSLGIPSSNPSLTRAASWLEHIQHEDGGWGESCHSSVE-KRFVT--LPFST
AaSCH    GTGAVVSALKAVGIDTREPYIQKALDWVEQHQNPDGGWGEDCRSYED-PAYAG--KGAST

GmSHC    ASQTAWALIGLLAAKRPKDREAIARGCQFLIERQE-DGSWTEEEY-TGTGFPGYGVGQAI
ZmSHC    PSQTAWALMGLIAANRPEDYEAIAKGCHYLIDRQEQDGSWKEEEF-TGTGFPGYGVGQTI
BspSHC   ASQTAWALMALLAANRPQDKDAIERGCMWLVERQS-AGTWDEPEF-TGTGFPGYGVGQTI
RpSHC    ASQTAWALMALIAADRPQDRDAIERGCLYLTETQR-DGTWQEVHY-TGTGFPGYGVGQTI
ScSHC    ASQTGWALMALLAAGE-RDSKAVERGVAWLAATQREDGSWDEPYF-TGTGFP--------
BamSHC   ASQTAWALLGLMAAGE-VNNPAVARGVEYLIAEQKEHGLWDETRF-TATGFP--------
BanSHC   PSQTAWALDALISYYD-TETPAIRKGVSYLL-----SNPYVNERYPTGTGLP--------
AaSCH    PSQTAWALMALIAGGR-AESEAARRGVQYLVETQRPDGGWDEPYY-TGTGFP--------

GmSHC    KLDDPSLPDRLLQGAELSRAFMLRYDLYRQYFPVMALSRA--RRMMKEDASAAA------
ZmSHC    KLDDPALSKRLLQGAELSRAFMLRYDFYRQFFPIMALSRA--ERLIDLNN----------
BspSHC   KLNDPALSQRLMQGPELSRAFMLRYGMYRHYFPLMALGRA--LRPQSHS-----------
RpSHC    KLNDPLLSKRLMQGPELSRSFMLRYDLYRHYFPMMAIGRV--LRQRGDRSGH--------
ScSHC    ------------------WDFSINYNLYRQVFPLTALGRYVHGEPFAKKPRAADAPAEAA
BamSHC   ------------------RVFYLRYHGYRKFFPLWALARY---RNLKRN---------NA
BanSHC   ------------------GAFYIRYHSYAHIYPLLTLAHY--IKKYRK------------
AaSCH    ------------------GDFYLGYTMYRHVFPTLALGRY--KQAIERR-----------

GmSHC    -------  (SEQ ID NO:2)
ZmSHC    -------  (SEQ ID NO:5)
BspSHC   -------  (SEQ ID NO:6)
RpSHC    -------  (SEQ ID NO:7)
ScSHC    PAEVKGS  (SEQ ID NO:8)
BamSHC   TRVTFGL  (SEQ ID NO:9)
BanSHC   -------  (SEQ ID NO:10)
AaSCH    -------  (SEQ ID NO:11)
```

*FIG. 1C*

SEQUENCE LISTING

<160> NUMBER OF SEQ ID NOS: 11

<210> SEQ ID NO 1
<211> LENGTH: 2058
<212> TYPE: DNA
<213> ORGANISM: Gluconobacter morbifer

<400> SEQUENCE: 1

| | | | | | | |
|---|---|---|---|---|---|---|
| atgagtccgg | cagatattag | caccaaaagc | agcagctttc | agcgtctgga | taacatgctg | 60 |
| ccggaagcag | ttagcagcgc | atgtgattgg | ctgattgatc | agcagaaacc | ggatggtcat | 120 |
| tgggttggtc | cggttgaaag | caatgcatgt | atggaagcac | agtggtgtct | ggcactgtgg | 180 |
| tttctgggtc | aagaagatca | tccgctgcgt | ccgcgtctgg | cacaggcact | gctggaaatg | 240 |
| cagcgtgaag | atggtagctg | gggtatttat | gttggtgcag | atcatggtga | tattaacacc | 300 |
| accgttgaag | catatgcagc | actgcgtagc | atgggttatg | cagcagatat | gccgattatg | 360 |
| gcaaaaagcg | cagcatggat | ccagcagaaa | ggtggtctgc | gtaatgttcg | tgttttacc | 420 |
| cgttattggc | tggcactgat | tggtgaatgg | ccgtgggata | aaccccgaa | tctgcctccg | 480 |
| gaaattatct | ggctgccgga | caattttatc | ttcagcattt | ataactttgc | ccagtgggca | 540 |
| cgtgcaacca | tgatgccgct | gaccattctg | agcgcacgtc | gtccgagccg | tccgctgctg | 600 |
| cctgaaaatc | gtctgatgg | tctgtttccg | gaaggtcgtg | aaaattttga | ttatgaactg | 660 |
| ccggttaaag | gcgaagagga | tctgtggggt | cgttttttc | gtgcagccga | taaaggtctg | 720 |
| catagcctgc | agagctttcc | ggttcgtcgt | tttgttccgc | gtgaagcagc | aattcgtcat | 780 |
| gttattgaat | ggattattcg | tcaccaggat | gcagatggtg | gttggggtgg | tattcagcct | 840 |
| ccgtggattt | atggtctgat | ggcactgagc | gttgaaggtt | atccgctgca | tcatccggtt | 900 |
| ctggcaaaag | caatggatgc | actgaatgat | cctggttggc | gtcgtgataa | aggtgatgca | 960 |
| agctggattc | aggcaaccaa | tagtccggtt | tgggatacca | tgctggcagt | tctggccctg | 1020 |
| catgatgcgg | gtgcagaaga | tcgttatagt | ccgcagatgg | ataaagcaat | tggttggctg | 1080 |
| ctggaccgtc | aggttcgtgt | gaaaggtgat | tggagcatta | aactgccgga | taccgaacct | 1140 |
| ggtggctggg | catttgaata | tgccaatgat | aaatatccgg | acaccgatga | taccgcagtt | 1200 |
| gccctgattg | cactggcagg | ttgtcgtcat | cgtccggaat | ggcgtgaacg | tgatattgaa | 1260 |
| ggtgcaatta | gccgtggtgt | gaattggctg | ttagcaatgc | agagcagctc | aggtggatgg | 1320 |
| ggtgcatttg | ataaagataa | taatcgtagc | atcctgacca | agattccgtt | ttgtgatttt | 1380 |
| ggtgaagcac | tggatccgcc | tagcgttgat | gttaccgcac | atgttctgga | agcatttggt | 1440 |
| ctgctgggta | ttagccgtaa | tcatccgagc | gttcagaaag | cactggcata | tattcgtagc | 1500 |
| gaacaagaac | gtaatggtgc | atggtttggc | cgttggggtg | ttaattatgt | ttatggtaca | 1560 |
| ggtgcagttc | tgcctgcgct | ggcagccatt | ggtgaagata | tgacccagcc | gtatattgtt | 1620 |
| cgtgcctgtg | attggttaat | gagcgtgcag | caagaaaatg | gcggttgggg | agaaagctgt | 1680 |
| gccagctata | tggatattaa | tgcagttggt | catggtgttg | caaccgcaag | ccagaccgca | 1740 |
| tgggctctga | ttggcctgct | ggcagcaaaa | cgtccgaaag | atcgtgaagc | aattgcacgt | 1800 |
| ggttgtcagt | ttctgattga | acgccaagaa | gatggaagtt | ggaccgaaga | agaatacacc | 1860 |
| ggcaccggtt | ttccaggtta | tggtgttggt | caggcaatta | aactgatga | tccgagcctg | 1920 |
| ccggatcgtc | tgctgcaggg | tgccgaactg | agccgtgcat | ttatgctgcg | ttatgatctg | 1980 |
| tatcgtcagt | attttccggt | gatggccctg | agtcgtgcac | gtcgtatgat | gaaagaagat | 2040 |
| gcaagcgcag | ccgcataa | | | | | 2058 |

<210> SEQ ID NO 2
<211> LENGTH: 685
<212> TYPE: PRT
<213> ORGANISM: Gluconobacter morbifer

<400> SEQUENCE: 2

| | | | | | | | | | | | | | | |
|---|---|---|---|---|---|---|---|---|---|---|---|---|---|---|
| Met | Ser | Pro | Ala | Asp | Ile | Ser | Thr | Lys | Ser | Ser | Phe | Gln | Arg | Leu |
| 1 | | | | 5 | | | | | 10 | | | | | 15 |
| Asp | Asn | Met | Leu | Pro | Glu | Ala | Val | Ser | Ser | Ala | Cys | Asp | Trp | Leu | Ile |
| | | | 20 | | | | | 25 | | | | | 30 | | |
| Asp | Gln | Gln | Lys | Pro | Asp | Gly | His | Trp | Val | Gly | Pro | Val | Glu | Ser | Asn |
| | | 35 | | | | | 40 | | | | | 45 | | | |
| Ala | Cys | Met | Glu | Ala | Gln | Trp | Cys | Leu | Ala | Leu | Trp | Phe | Leu | Gly | Gln |
| | 50 | | | | | 55 | | | | | 60 | | | | |
| Glu | Asp | His | Pro | Leu | Arg | Pro | Arg | Leu | Ala | Gln | Ala | Leu | Leu | Glu | Met |
| 65 | | | | | 70 | | | | | 75 | | | | | 80 |
| Gln | Arg | Glu | Asp | Gly | Ser | Trp | Gly | Ile | Tyr | Val | Gly | Ala | Asp | His | Gly |
| | | | | 85 | | | | | 90 | | | | | 95 | |
| Asp | Ile | Asn | Thr | Thr | Val | Glu | Ala | Tyr | Ala | Ala | Leu | Arg | Ser | Met | Gly |
| | | | 100 | | | | | 105 | | | | | 110 | | |
| Tyr | Ala | Ala | Asp | Met | Pro | Ile | Met | Ala | Lys | Ser | Ala | Ala | Trp | Ile | Gln |
| | | 115 | | | | | 120 | | | | | 125 | | | |
| Gln | Lys | Gly | Gly | Leu | Arg | Asn | Val | Arg | Val | Phe | Thr | Arg | Tyr | Trp | Leu |
| | 130 | | | | | 135 | | | | | 140 | | | | |
| Ala | Leu | Ile | Gly | Glu | Trp | Pro | Trp | Asp | Lys | Thr | Pro | Asn | Leu | Pro | Pro |
| 145 | | | | | 150 | | | | | 155 | | | | | 160 |
| Glu | Ile | Ile | Trp | Leu | Pro | Asp | Asn | Phe | Ile | Phe | Ser | Ile | Tyr | Asn | Phe |
| | | | | 165 | | | | | 170 | | | | | 175 | |
| Ala | Gln | Trp | Ala | Arg | Ala | Thr | Met | Met | Pro | Leu | Thr | Ile | Leu | Ser | Ala |
| | | | 180 | | | | | 185 | | | | | 190 | | |
| Arg | Arg | Pro | Ser | Arg | Pro | Leu | Leu | Pro | Glu | Asn | Arg | Leu | Asp | Gly | Leu |
| | | 195 | | | | | 200 | | | | | 205 | | | |
| Phe | Pro | Glu | Gly | Arg | Glu | Asn | Phe | Asp | Tyr | Glu | Leu | Pro | Val | Lys | Gly |
| | 210 | | | | | 215 | | | | | 220 | | | | |
| Glu | Glu | Asp | Leu | Trp | Gly | Arg | Phe | Phe | Arg | Ala | Ala | Asp | Lys | Gly | Leu |
| 225 | | | | | 230 | | | | | 235 | | | | | 240 |
| His | Ser | Leu | Gln | Ser | Phe | Pro | Val | Arg | Arg | Phe | Val | Pro | Arg | Glu | Ala |
| | | | | 245 | | | | | 250 | | | | | 255 | |
| Ala | Ile | Arg | His | Val | Ile | Glu | Trp | Ile | Ile | Arg | His | Gln | Asp | Ala | Asp |
| | | | 260 | | | | | 265 | | | | | 270 | | |
| Gly | Gly | Trp | Gly | Gly | Ile | Gln | Pro | Pro | Trp | Ile | Tyr | Gly | Leu | Met | Ala |
| | | 275 | | | | | 280 | | | | | 285 | | | |
| Leu | Ser | Val | Glu | Gly | Tyr | Pro | Leu | His | His | Pro | Val | Leu | Ala | Lys | Ala |
| | 290 | | | | | 295 | | | | | 300 | | | | |
| Met | Asp | Ala | Leu | Asn | Asp | Pro | Gly | Trp | Arg | Arg | Asp | Lys | Gly | Asp | Ala |
| 305 | | | | | 310 | | | | | 315 | | | | | 320 |
| Ser | Trp | Ile | Gln | Ala | Thr | Asn | Ser | Pro | Val | Trp | Asp | Thr | Met | Leu | Ala |
| | | | | 325 | | | | | 330 | | | | | 335 | |
| Val | Leu | Ala | Leu | His | Asp | Ala | Gly | Ala | Glu | Asp | Arg | Tyr | Ser | Pro | Gln |
| | | | 340 | | | | | 345 | | | | | 350 | | |
| Met | Asp | Lys | Ala | Ile | Gly | Trp | Leu | Leu | Asp | Arg | Gln | Val | Arg | Val | Lys |
| | | 355 | | | | | 360 | | | | | 365 | | | |
| Gly | Asp | Trp | Ser | Ile | Lys | Leu | Pro | Asp | Thr | Glu | Pro | Gly | Gly | Trp | Ala |

```
                370                 375                 380
Phe Glu Tyr Ala Asn Asp Lys Tyr Pro Asp Thr Asp Thr Ala Val
385                 390                 395                 400

Ala Leu Ile Ala Leu Ala Gly Cys Arg His Arg Pro Glu Trp Arg Glu
                405                 410                 415

Arg Asp Ile Glu Gly Ala Ile Ser Arg Gly Val Asn Trp Leu Leu Ala
                420                 425                 430

Met Gln Ser Ser Gly Gly Trp Gly Ala Phe Asp Lys Asp Asn Asn
                435                 440                 445

Arg Ser Ile Leu Thr Lys Ile Pro Phe Cys Asp Phe Gly Glu Ala Leu
                450                 455                 460

Asp Pro Pro Ser Val Asp Val Thr Ala His Val Leu Glu Ala Phe Gly
465                 470                 475                 480

Leu Leu Gly Ile Ser Arg Asn His Pro Ser Val Gln Lys Ala Leu Ala
                485                 490                 495

Tyr Ile Arg Ser Glu Gln Glu Arg Asn Gly Ala Trp Phe Gly Arg Trp
                500                 505                 510

Gly Val Asn Tyr Val Tyr Gly Thr Gly Ala Val Leu Pro Ala Leu Ala
                515                 520                 525

Ala Ile Gly Glu Asp Met Thr Gln Pro Tyr Ile Val Arg Ala Cys Asp
530                 535                 540

Trp Leu Met Ser Val Gln Gln Glu Asn Gly Gly Trp Gly Glu Ser Cys
545                 550                 555                 560

Ala Ser Tyr Met Asp Ile Asn Ala Val Gly His Gly Val Ala Thr Ala
                565                 570                 575

Ser Gln Thr Ala Trp Ala Leu Ile Gly Leu Leu Ala Ala Lys Arg Pro
                580                 585                 590

Lys Asp Arg Glu Ala Ile Ala Arg Gly Cys Gln Phe Leu Ile Glu Arg
                595                 600                 605

Gln Glu Asp Gly Ser Trp Thr Glu Glu Tyr Thr Gly Thr Gly Phe
                610                 615                 620

Pro Gly Tyr Gly Val Gly Gln Ala Ile Lys Leu Asp Asp Pro Ser Leu
625                 630                 635                 640

Pro Asp Arg Leu Leu Gln Gly Ala Glu Leu Ser Arg Ala Phe Met Leu
                645                 650                 655

Arg Tyr Asp Leu Tyr Arg Gln Tyr Phe Pro Val Met Ala Leu Ser Arg
                660                 665                 670

Ala Arg Arg Met Met Lys Glu Asp Ala Ser Ala Ala Ala
                675                 680                 685

<210> SEQ ID NO 3
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 3

Gln Xaa Xaa Xaa Gly Xaa Trp
1               5
```

-continued

```
<210> SEQ ID NO 4
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 4

Asp Xaa Asp Asp Thr Ala
1               5

<210> SEQ ID NO 5
<211> LENGTH: 725
<212> TYPE: PRT
<213> ORGANISM: Zymomonas mobilis

<400> SEQUENCE: 5

Met Gly Ile Asp Arg Met Asn Ser Leu Ser Arg Leu Met Lys Lys
1               5                   10                  15

Ile Phe Gly Ala Glu Lys Thr Ser Tyr Lys Pro Ala Ser Asp Thr Ile
                20                  25                  30

Ile Gly Thr Asp Thr Leu Lys Arg Pro Asn Arg Pro Glu Pro Thr
            35                  40                  45

Ala Lys Val Asp Lys Thr Ile Phe Lys Thr Met Gly Asn Ser Leu Asn
        50                  55                  60

Asn Thr Leu Val Ser Ala Cys Asp Trp Leu Ile Gly Gln Gln Lys Pro
65                  70                  75                  80

Asp Gly His Trp Val Gly Ala Val Glu Ser Asn Ala Ser Met Glu Ala
                85                  90                  95

Glu Trp Cys Leu Ala Leu Trp Phe Leu Gly Leu Glu Asp His Pro Leu
            100                 105                 110

Arg Pro Arg Leu Gly Asn Ala Leu Leu Glu Met Gln Arg Glu Asp Gly
        115                 120                 125

Ser Trp Gly Val Tyr Phe Gly Ala Gly Asn Gly Asp Ile Asn Ala Thr
    130                 135                 140

Val Glu Ala Tyr Ala Ala Leu Arg Ser Leu Gly Tyr Ser Ala Asp Asn
145                 150                 155                 160

Pro Val Leu Lys Lys Ala Ala Ala Trp Ile Ala Glu Lys Gly Gly Leu
                165                 170                 175

Lys Asn Ile Arg Val Phe Thr Arg Tyr Trp Leu Ala Leu Ile Gly Glu
            180                 185                 190

Trp Pro Trp Glu Lys Thr Pro Asn Leu Pro Pro Glu Ile Ile Trp Phe
        195                 200                 205

Pro Asp Asn Phe Val Phe Ser Ile Tyr Asn Phe Ala Gln Trp Ala Arg
    210                 215                 220

Ala Thr Met Val Pro Ile Ala Ile Leu Ser Ala Arg Arg Pro Ser Arg
225                 230                 235                 240

Pro Leu Arg Pro Gln Asp Arg Leu Asp Glu Leu Phe Pro Glu Gly Arg
                245                 250                 255

Ala Arg Phe Asp Tyr Glu Leu Pro Lys Lys Glu Gly Ile Asp Leu Trp
            260                 265                 270

Ser Gln Phe Phe Arg Thr Thr Asp Arg Gly Leu His Trp Val Gln Ser
        275                 280                 285
```

```
Asn Leu Leu Lys Arg Asn Ser Leu Arg Glu Ala Ala Ile Arg His Val
    290                 295                 300

Leu Glu Trp Ile Ile Arg His Gln Asp Ala Asp Gly Gly Trp Gly Gly
305                 310                 315                 320

Ile Gln Pro Pro Trp Val Tyr Gly Leu Met Ala Leu His Gly Glu Gly
                325                 330                 335

Tyr Gln Leu Tyr His Pro Val Met Ala Lys Ala Leu Ser Ala Leu Asp
            340                 345                 350

Asp Pro Gly Trp Arg His Asp Arg Gly Glu Ser Ser Trp Ile Gln Ala
        355                 360                 365

Thr Asn Ser Pro Val Trp Asp Thr Met Leu Ala Leu Met Ala Leu Lys
370                 375                 380

Asp Ala Lys Ala Glu Asp Arg Phe Thr Pro Glu Met Asp Lys Ala Ala
385                 390                 395                 400

Asp Trp Leu Leu Ala Arg Gln Val Lys Val Lys Gly Asp Trp Ser Ile
                405                 410                 415

Lys Leu Pro Asp Val Glu Pro Gly Gly Trp Ala Phe Glu Tyr Ala Asn
                420                 425                 430

Asp Arg Tyr Pro Asp Thr Asp Thr Ala Val Ala Leu Ile Ala Leu
                435                 440                 445

Ser Ser Tyr Arg Asp Lys Glu Glu Trp Gln Lys Lys Gly Val Glu Asp
450                 455                 460

Ala Ile Thr Arg Gly Val Asn Trp Leu Ile Ala Met Gln Ser Glu Cys
465                 470                 475                 480

Gly Gly Trp Gly Ala Phe Asp Lys Asp Asn Asn Arg Ser Ile Leu Ser
                485                 490                 495

Lys Ile Pro Phe Cys Asp Phe Gly Glu Ser Ile Asp Pro Pro Ser Val
                500                 505                 510

Asp Val Thr Ala His Val Leu Glu Ala Phe Gly Thr Leu Gly Leu Ser
                515                 520                 525

Arg Asp Met Pro Val Ile Gln Lys Ala Ile Asp Tyr Val Arg Ser Glu
530                 535                 540

Gln Glu Ala Glu Gly Ala Trp Phe Gly Arg Trp Gly Val Asn Tyr Ile
545                 550                 555                 560

Tyr Gly Thr Gly Ala Val Leu Pro Ala Leu Ala Ala Ile Gly Glu Asp
                565                 570                 575

Met Thr Gln Pro Tyr Ile Thr Lys Ala Cys Asp Trp Leu Val Ala His
                580                 585                 590

Gln Gln Glu Asp Gly Gly Trp Gly Glu Ser Cys Ser Ser Tyr Met Glu
            595                 600                 605

Ile Asp Ser Ile Gly Lys Gly Pro Thr Thr Pro Ser Gln Thr Ala Trp
610                 615                 620

Ala Leu Met Gly Leu Ile Ala Ala Asn Arg Pro Glu Asp Tyr Glu Ala
625                 630                 635                 640

Ile Ala Lys Gly Cys His Tyr Leu Ile Asp Arg Gln Glu Gln Asp Gly
                645                 650                 655

Ser Trp Lys Glu Glu Phe Thr Gly Thr Gly Phe Pro Gly Tyr Gly
            660                 665                 670

Val Gly Gln Thr Ile Lys Leu Asp Asp Pro Ala Leu Ser Lys Arg Leu
        675                 680                 685

Leu Gln Gly Ala Glu Leu Ser Arg Ala Phe Met Leu Arg Tyr Asp Phe
    690                 695                 700
```

Tyr Arg Gln Phe Phe Pro Ile Met Ala Leu Ser Arg Ala Glu Arg Leu
705                 710                 715                 720

Ile Asp Leu Asn Asn
            725

<210> SEQ ID NO 6
<211> LENGTH: 684
<212> TYPE: PRT
<213> ORGANISM: Bradyrhizobium sp.

<400> SEQUENCE: 6

Met Thr Val Thr Ser Ala Ser Ala Arg Ala Thr Arg Asp Pro Gly
1               5                   10                  15

Asn Tyr Gln Thr Ala Leu Gln Ser Thr Val Arg Ala Ala Asp Trp
                20                  25                  30

Leu Ile Ala Asn Gln Lys Pro Asp Gly His Trp Val Gly Arg Ala Glu
            35                  40                  45

Ser Asn Ala Cys Met Glu Ala Gln Trp Cys Leu Ala Leu Trp Phe Met
50                  55                  60

Gly Leu Glu Asp His Pro Leu Arg Lys Arg Leu Gly Gln Ser Leu Leu
65                  70                  75                  80

Asp Ser Gln Arg Pro Asp Gly Ala Trp Gln Val Tyr Phe Gly Ala Pro
                85                  90                  95

Asn Gly Asp Ile Asn Ala Thr Val Glu Ala Tyr Ala Ala Leu Arg Ser
            100                 105                 110

Leu Gly Phe Arg Asp Asp Glu Pro Ala Val Arg Arg Ala Arg Glu Trp
        115                 120                 125

Ile Glu Ala Lys Gly Gly Leu Arg Asn Ile Arg Val Phe Thr Arg Tyr
130                 135                 140

Trp Leu Ala Leu Ile Gly Glu Trp Pro Trp Lys Thr Pro Asn Ile
145                 150                 155                 160

Pro Pro Glu Val Ile Trp Phe Pro Leu Trp Phe Pro Phe Ser Ile Tyr
                165                 170                 175

Asn Phe Ala Gln Trp Ala Arg Ala Thr Leu Met Pro Ile Ala Val Leu
            180                 185                 190

Ser Ala Arg Arg Pro Ser Arg Pro Leu Pro Pro Glu Asn Arg Leu Asp
        195                 200                 205

Ala Leu Phe Pro His Gly Arg Lys Ala Phe Asp Tyr Glu Leu Pro Val
210                 215                 220

Lys Ala Gly Ala Gly Trp Asp Arg Phe Phe Arg Gly Ala Asp Lys
225                 230                 235                 240

Val Leu His Lys Leu Gln Asn Leu Gly Asn Arg Leu Asn Leu Gly Leu
                245                 250                 255

Phe Arg Pro Ala Ala Thr Ser Arg Val Leu Glu Trp Met Ile Arg His
            260                 265                 270

Gln Asp Phe Asp Gly Ala Trp Gly Gly Ile Gln Pro Pro Trp Ile Tyr
        275                 280                 285

Gly Leu Met Ala Leu Tyr Ala Glu Gly Tyr Pro Leu Asn His Pro Val
290                 295                 300

Leu Ala Lys Gly Leu Asp Ala Leu Asn Asp Pro Gly Trp Arg Val Asp
305                 310                 315                 320

Val Gly Asp Ala Thr Tyr Ile Gln Ala Thr Asn Ser Pro Val Trp Asp
                325                 330                 335

Thr Ile Leu Thr Leu Leu Ala Phe Asp Asp Ala Gly Val Leu Gly Asp
            340                 345                 350

Tyr Pro Glu Ala Val Asp Lys Ala Val Asp Trp Val Leu Gln Arg Gln
        355                 360                 365

Val Arg Val Pro Gly Asp Trp Ser Met Lys Leu Pro His Val Lys Pro
    370                 375                 380

Gly Gly Trp Ala Phe Glu Tyr Ala Asn Asn Tyr Tyr Pro Asp Thr Asp
385                 390                 395                 400

Asp Thr Ala Val Ala Leu Ile Ala Leu Ala Pro Leu Arg His Asp Pro
                405                 410                 415

Lys Trp Lys Ala Lys Gly Ile Asp Glu Ala Ile Gln Leu Gly Val Asp
                420                 425                 430

Trp Leu Ile Gly Met Gln Ser Gln Gly Gly Trp Gly Ala Phe Asp
        435                 440                 445

Lys Asp Asn Asn Gln Lys Ile Leu Thr Lys Ile Pro Phe Cys Asp Tyr
        450                 455                 460

Gly Glu Ala Leu Asp Pro Pro Ser Val Asp Val Thr Ala His Ile Ile
465                 470                 475                 480

Glu Ala Phe Gly Lys Leu Gly Ile Ser Arg Asn His Pro Ser Met Val
                485                 490                 495

Gln Ala Leu Asp Tyr Ile Arg Arg Glu Gln Glu Pro Ser Gly Pro Trp
            500                 505                 510

Phe Gly Arg Trp Gly Val Asn Tyr Val Tyr Gly Thr Gly Ala Val Leu
        515                 520                 525

Pro Ala Leu Ala Ala Ile Gly Glu Asp Met Thr Gln Pro Tyr Ile Gly
    530                 535                 540

Arg Ala Cys Asp Trp Leu Val Ala His Gln Gln Ala Asp Gly Gly Trp
545                 550                 555                 560

Gly Glu Ser Cys Ala Ser Tyr Met Asp Val Ser Ala Val Gly Arg Gly
                565                 570                 575

Thr Thr Thr Ala Ser Gln Thr Ala Trp Ala Leu Met Ala Leu Leu Ala
            580                 585                 590

Ala Asn Arg Pro Gln Asp Lys Asp Ala Ile Glu Arg Gly Cys Met Trp
        595                 600                 605

Leu Val Glu Arg Gln Ser Ala Gly Thr Trp Asp Glu Pro Glu Phe Thr
    610                 615                 620

Gly Thr Gly Phe Pro Gly Tyr Gly Val Gly Gln Thr Ile Lys Leu Asn
625                 630                 635                 640

Asp Pro Ala Leu Ser Gln Arg Leu Met Gln Gly Pro Glu Leu Ser Arg
                645                 650                 655

Ala Phe Met Leu Arg Tyr Gly Met Tyr Arg His Tyr Phe Pro Leu Met
            660                 665                 670

Ala Leu Gly Arg Ala Leu Arg Pro Gln Ser His Ser
        675                 680

<210> SEQ ID NO 7
<211> LENGTH: 685
<212> TYPE: PRT
<213> ORGANISM: Rhodopseudomonas palustris

<400> SEQUENCE: 7

Met Asp Ser Ile Leu Ala Pro Arg Ala Asp Ala Pro Arg Asn Ile Asp
1               5                   10                  15

Gly Ala Leu Arg Glu Ser Val Gln Gln Ala Ala Asp Trp Leu Val Ala
            20                  25                  30

Asn Gln Lys Pro Asp Gly His Trp Val Gly Arg Ala Glu Thr Asn Ala

```
            35                  40                  45
Thr Met Glu Ala Gln Trp Cys Leu Ala Leu Trp Phe Leu Gly Leu Glu
 50                  55                  60

Asp His Pro Leu Arg Val Arg Leu Gly Arg Ala Leu Leu Asp Thr Gln
 65                  70                  75                  80

Arg Pro Asp Gly Ala Trp His Val Phe Tyr Gly Ala Pro Asn Gly Asp
                 85                  90                  95

Ile Asn Ala Thr Val Glu Ala Tyr Ala Ala Leu Arg Ser Leu Gly His
                100                 105                 110

Arg Asp Asp Glu Glu Pro Leu Arg Lys Ala Arg Asp Trp Ile Leu Ser
            115                 120                 125

Lys Gly Gly Leu Ala Asn Ile Arg Val Phe Thr Arg Tyr Trp Leu Ala
130                 135                 140

Leu Ile Gly Glu Trp Pro Trp Glu Lys Thr Pro Asn Ile Leu Pro Glu
145                 150                 155                 160

Val Ile Trp Leu Pro Thr Trp Phe Pro Phe Ser Ile Tyr Asn Phe Ala
                165                 170                 175

Gln Trp Ala Arg Ala Thr Leu Met Pro Ile Ala Val Leu Ser Ala His
                180                 185                 190

Arg Pro Ser Arg Pro Leu Ala Pro Gln Asp Arg Leu Asp Ala Leu Phe
            195                 200                 205

Pro Gln Gly Arg Asp Ser Phe Asn Tyr Asp Leu Pro Ala Arg Leu Gly
210                 215                 220

Ala Gly Val Trp Asp Val Ile Phe Arg Lys Ile Asp Thr Ile Leu His
225                 230                 235                 240

Arg Leu Gln Asp Trp Gly Ala Arg Arg Gly Pro His Gly Ile Met Arg
                245                 250                 255

Arg Gly Ala Ile Asp His Val Leu Gln Trp Ile Arg His Gln Asp
                260                 265                 270

Tyr Asp Gly Ser Trp Gly Gly Ile Gln Pro Pro Trp Ile Tyr Gly Leu
            275                 280                 285

Met Ala Leu His Thr Glu Gly Tyr Ala Met Thr His Pro Val Met Ala
290                 295                 300

Lys Ala Leu Asp Ala Leu Asn Glu Pro Gly Trp Arg Ile Asp Ile Gly
305                 310                 315                 320

Asp Ala Thr Phe Ile Gln Ala Thr Asn Ser Pro Val Trp Asp Thr Met
                325                 330                 335

Leu Ser Leu Leu Ala Phe Asp Asp Ala Gly Leu Gly Glu Arg Tyr Pro
                340                 345                 350

Glu Gln Val Glu Arg Ala Val Arg Trp Val Leu Lys Arg Gln Val Leu
            355                 360                 365

Val Pro Gly Asp Trp Ser Val Lys Leu Pro Asp Val Lys Pro Gly Gly
370                 375                 380

Trp Ala Phe Glu Tyr Ala Asn Asn Phe Tyr Pro Asp Thr Asp Thr
385                 390                 395                 400

Ser Val Ala Leu Met Ala Leu Ala Pro Phe Arg His Asp Pro Lys Trp
                405                 410                 415

Gln Ala Glu Gly Ile Glu Asp Ala Ile Gln Arg Gly Ile Asp Trp Leu
                420                 425                 430

Val Ala Met Gln Cys Lys Glu Gly Gly Trp Gly Ala Phe Asp Lys Asp
            435                 440                 445

Asn Asp Lys Lys Ile Leu Ala Lys Ile Pro Phe Cys Asp Phe Gly Glu
450                 455                 460
```

```
Ala Leu Asp Pro Pro Ser Ala Asp Val Thr Ala His Ile Ile Glu Ala
465                 470                 475                 480

Phe Ala Lys Val Gly Leu Asp Arg Asn His Pro Ser Ile Val Arg Ala
            485                 490                 495

Leu Asp Tyr Leu Lys Arg Glu Gln Glu Pro Glu Gly Pro Trp Phe Gly
            500                 505                 510

Arg Trp Gly Val Asn Tyr Val Tyr Gly Thr Gly Ala Val Leu Pro Ala
            515                 520                 525

Leu Ala Ala Ile Gly Glu Asp Met Arg Gln Pro Tyr Ile Ala Arg Ala
530                 535                 540

Cys Asp Trp Leu Ile Ala Arg Gln Gln Ala Asn Gly Gly Trp Gly Glu
545                 550                 555                 560

Ser Cys Val Ser Tyr Met Asp Ala Lys Gln Ala Gly Glu Gly Thr Ala
            565                 570                 575

Thr Ala Ser Gln Thr Ala Trp Ala Leu Met Ala Leu Ile Ala Ala Asp
            580                 585                 590

Arg Pro Gln Asp Arg Asp Ala Ile Glu Arg Gly Cys Leu Tyr Leu Thr
            595                 600                 605

Glu Thr Gln Arg Asp Gly Thr Trp Gln Glu Val His Tyr Thr Gly Thr
610                 615                 620

Gly Phe Pro Gly Tyr Gly Val Gly Gln Thr Ile Lys Leu Asn Asp Pro
625                 630                 635                 640

Leu Leu Ser Lys Arg Leu Met Gln Gly Pro Glu Leu Ser Arg Ser Phe
            645                 650                 655

Met Leu Arg Tyr Asp Leu Tyr Arg His Tyr Phe Pro Met Met Ala Ile
            660                 665                 670

Gly Arg Val Leu Arg Gln Arg Gly Asp Arg Ser Gly His
            675                 680                 685

<210> SEQ ID NO 8
<211> LENGTH: 680
<212> TYPE: PRT
<213> ORGANISM: Streptomyces coelicolor

<400> SEQUENCE: 8

Met Thr Ala Thr Thr Asp Gly Ser Thr Gly Ala Ser Leu Arg Pro Leu
1               5                   10                  15

Ala Ala Ser Ala Ser Asp Thr Asp Ile Thr Ile Pro Ala Ala Ala Ala
                20                  25                  30

Gly Val Pro Glu Ala Ala Arg Ala Thr Arg Arg Ala Thr Asp Phe
            35                  40                  45

Leu Leu Ala Lys Gln Asp Ala Glu Gly Trp Trp Lys Gly Asp Leu Glu
50                  55                  60

Thr Asn Val Thr Met Asp Ala Glu Asp Leu Leu Leu Arg Gln Phe Leu
65                  70                  75                  80

Gly Ile Gln Asp Glu Glu Thr Thr Arg Ala Ala Ala Leu Phe Ile Arg
                85                  90                  95

Gly Glu Gln Arg Glu Asp Gly Thr Trp Ala Thr Phe Tyr Gly Gly Pro
            100                 105                 110

Gly Glu Leu Ser Thr Thr Ile Glu Ala Tyr Val Ala Leu Arg Leu Ala
            115                 120                 125

Gly Asp Ser Pro Glu Ala Pro His Met Ala Arg Ala Ala Glu Trp Ile
130                 135                 140

Arg Ser Arg Gly Gly Ile Ala Ser Ala Arg Val Phe Thr Arg Ile Trp
```

```
            145                 150                 155                 160
Leu Ala Leu Phe Gly Trp Trp Lys Trp Asp Asp Leu Pro Glu Leu Pro
                    165                 170                 175
Pro Glu Leu Ile Tyr Phe Pro Thr Trp Val Pro Leu Asn Ile Tyr Asp
                    180                 185                 190
Phe Gly Cys Trp Ala Arg Gln Thr Ile Val Pro Leu Thr Ile Val Ser
                    195                 200                 205
Ala Lys Arg Pro Val Arg Pro Ala Pro Phe Pro Leu Asp Glu Leu His
                    210                 215                 220
Thr Asp Pro Ala Arg Pro Asn Pro Pro Arg Pro Leu Ala Pro Val Ala
225                 230                 235                 240
Ser Trp Asp Gly Ala Phe Gln Arg Ile Asp Lys Ala Leu His Ala Tyr
                    245                 250                 255
Arg Lys Val Ala Pro Arg Arg Leu Arg Arg Ala Ala Met Asn Ser Ala
                    260                 265                 270
Ala Arg Trp Ile Ile Glu Arg Gln Glu Asn Asp Gly Cys Trp Gly Gly
                    275                 280                 285
Ile Gln Pro Pro Ala Val Tyr Ser Val Ile Ala Leu Tyr Leu Leu Gly
                    290                 295                 300
Tyr Asp Leu Glu His Pro Val Met Arg Ala Gly Leu Glu Ser Leu Asp
305                 310                 315                 320
Arg Phe Ala Val Trp Arg Glu Asp Gly Ala Arg Met Ile Glu Ala Cys
                    325                 330                 335
Gln Ser Pro Val Trp Asp Thr Cys Leu Ala Thr Ile Ala Leu Ala Asp
                    340                 345                 350
Ala Gly Val Pro Glu Asp His Pro Gln Leu Val Lys Ala Ser Asp Trp
                    355                 360                 365
Met Leu Gly Glu Gln Ile Val Arg Pro Gly Asp Trp Ser Val Lys Arg
                    370                 375                 380
Pro Gly Leu Pro Pro Gly Gly Trp Ala Phe Glu Phe His Asn Asp Asn
385                 390                 395                 400
Tyr Pro Asp Ile Asp Asp Thr Ala Glu Val Val Leu Ala Leu Arg Arg
                    405                 410                 415
Val Arg His His Asp Pro Glu Arg Val Glu Lys Ala Ile Gly Arg Gly
                    420                 425                 430
Val Arg Trp Asn Leu Gly Met Gln Ser Lys Asn Gly Ala Trp Gly Ala
                    435                 440                 445
Phe Asp Val Asp Asn Thr Ser Ala Phe Pro Asn Arg Leu Pro Phe Cys
                    450                 455                 460
Asp Phe Gly Glu Val Ile Asp Pro Pro Ser Ala Asp Val Thr Ala His
465                 470                 475                 480
Val Val Glu Met Leu Ala Val Glu Gly Leu Ala His Asp Pro Arg Thr
                    485                 490                 495
Arg Arg Gly Ile Gln Trp Leu Leu Asp Ala Gln Glu Thr Asp Gly Ser
                    500                 505                 510
Trp Phe Gly Arg Trp Gly Val Asn Tyr Val Tyr Gly Thr Gly Ser Val
                    515                 520                 525
Ile Pro Ala Leu Thr Ala Ala Gly Leu Pro Thr Ser His Pro Ala Ile
                    530                 535                 540
Arg Arg Ala Val Arg Trp Leu Glu Ser Val Gln Asn Glu Asp Gly Gly
545                 550                 555                 560
Trp Gly Glu Asp Leu Arg Ser Tyr Arg Tyr Val Arg Glu Trp Ser Gly
                    565                 570                 575
```

```
Arg Gly Ala Ser Thr Ala Ser Gln Thr Gly Trp Ala Leu Met Ala Leu
            580                 585                 590

Leu Ala Ala Gly Glu Arg Asp Ser Lys Ala Val Glu Arg Gly Val Ala
            595                 600                 605

Trp Leu Ala Ala Thr Gln Arg Glu Asp Gly Ser Trp Asp Pro Tyr
            610                 615                 620

Phe Thr Gly Thr Gly Phe Pro Trp Asp Phe Ser Ile Asn Tyr Asn Leu
625                 630                 635                 640

Tyr Arg Gln Val Phe Pro Leu Thr Ala Leu Gly Arg Tyr Val His Gly
                645                 650                 655

Glu Pro Phe Ala Lys Lys Pro Arg Ala Ala Asp Ala Pro Ala Glu Ala
            660                 665                 670

Ala Pro Ala Glu Val Lys Gly Ser
            675                 680

<210> SEQ ID NO 9
<211> LENGTH: 657
<212> TYPE: PRT
<213> ORGANISM: Burkholderia ambifaria

<400> SEQUENCE: 9

Met Asn Asp Leu Thr Glu Met Ala Thr Leu Ser Ala Gly Thr Val Pro
1               5                   10                  15

Ala Gly Leu Asp Ala Ala Val Ala Ser Ala Thr Asp Ala Leu Leu Ala
            20                  25                  30

Ala Gln Asn Ala Asp Gly His Trp Val Tyr Glu Leu Glu Ala Asp Ser
        35                  40                  45

Thr Ile Pro Ala Glu Tyr Val Leu Leu Val His Tyr Leu Gly Glu Thr
    50                  55                  60

Pro Asn Leu Glu Leu Glu Gln Lys Ile Gly Arg Tyr Leu Arg Arg Val
65              70                  75                  80

Gln Gln Ala Asp Gly Gly Trp Pro Leu Phe Thr Asp Gly Ala Pro Asn
            85                  90                  95

Ile Ser Ala Ser Val Lys Ala Tyr Phe Ala Leu Lys Val Ile Gly Asp
            100                 105                 110

Asp Glu Asn Ala Glu His Met Gln Arg Ala Arg Arg Ala Ile Gln Ala
        115                 120                 125

Met Gly Gly Ala Glu Met Ser Asn Val Phe Thr Arg Ile Gln Leu Ala
    130                 135                 140

Leu Tyr Gly Ala Ile Pro Trp Arg Ala Val Pro Met Met Pro Val Glu
145                 150                 155                 160

Ile Met Leu Leu Pro Gln Trp Phe Pro Phe His Leu Ser Lys Val Ser
                165                 170                 175

Tyr Trp Ala Arg Thr Val Ile Val Pro Leu Leu Val Leu Asn Ala Lys
            180                 185                 190

Arg Pro Ile Ala Lys Asn Pro Arg Gly Val Arg Ile Asp Glu Leu Phe
        195                 200                 205

Val Asp Pro Pro Val Asn Ala Gly Leu Leu Pro Arg Gln Gly His Gln
    210                 215                 220

Ser Pro Gly Trp Phe Ala Phe Phe Arg Val Val Asp His Ala Leu Arg
225                 230                 235                 240

Ala Ala Asp Gly Leu Phe Pro Asn Tyr Thr Arg Glu Arg Ala Ile Arg
                245                 250                 255

Gln Ala Val Ser Phe Val Asp Glu Arg Leu Asn Gly Glu Asp Gly Leu
```

```
            260                 265                 270
Gly Ala Ile Tyr Pro Ala Met Ala Asn Ala Val Met Met Tyr Asp Val
            275                 280                 285
Leu Gly Tyr Ala Glu Asp His Pro Asn Arg Ala Ile Ala Arg Lys Ser
            290                 295                 300
Ile Glu Lys Leu Leu Val Val Gln Glu Asp Glu Ala Tyr Cys Gln Pro
305                 310                 315                 320
Cys Leu Ser Pro Val Trp Asp Thr Ser Leu Ala Ala His Ala Leu Leu
                325                 330                 335
Glu Thr Gly Asp Ala Arg Ala Glu Glu Ala Val Ile Arg Gly Leu Glu
            340                 345                 350
Trp Leu Arg Pro Leu Gln Ile Leu Asp Val Arg Gly Asp Trp Ile Ser
            355                 360                 365
Arg Arg Pro His Val Arg Pro Gly Gly Trp Ala Phe Gln Tyr Ala Asn
            370                 375                 380
Pro His Tyr Pro Asp Val Asp Asp Thr Ala Val Val Ala Val Ala Met
385                 390                 395                 400
Asp Arg Val Gln Lys Leu Lys His Asn Asp Ala Phe Arg Asp Ser Ile
                405                 410                 415
Ala Arg Ala Arg Glu Trp Val Val Gly Met Gln Ser Ser Asp Gly Gly
            420                 425                 430
Trp Gly Ala Phe Glu Pro Glu Asn Thr Gln Tyr Tyr Leu Asn Asn Ile
            435                 440                 445
Pro Phe Ser Asp His Gly Ala Leu Leu Asp Pro Pro Thr Ala Asp Val
            450                 455                 460
Ser Gly Arg Cys Leu Ser Met Leu Ala Gln Leu Gly Glu Thr Pro Leu
465                 470                 475                 480
Asn Ser Glu Pro Ala Arg Arg Ala Leu Asp Tyr Met Leu Lys Glu Gln
                485                 490                 495
Glu Pro Asp Gly Ser Trp Tyr Gly Arg Trp Gly Met Asn Tyr Val Tyr
                500                 505                 510
Gly Thr Trp Thr Ala Leu Cys Ala Leu Asn Ala Ala Gly Leu Thr Pro
            515                 520                 525
Asp Asp Pro Arg Val Lys Arg Gly Ala Gln Trp Leu Leu Ser Ile Gln
            530                 535                 540
Asn Lys Asp Gly Gly Trp Gly Glu Asp Gly Asp Ser Tyr Lys Leu Asn
545                 550                 555                 560
Tyr Arg Gly Phe Glu Gln Ala Pro Ser Thr Ala Ser Gln Thr Ala Trp
                565                 570                 575
Ala Leu Leu Gly Leu Met Ala Ala Gly Glu Val Asn Asn Pro Ala Val
            580                 585                 590
Ala Arg Gly Val Glu Tyr Leu Ile Ala Glu Gln Lys Glu His Gly Leu
            595                 600                 605
Trp Asp Glu Thr Arg Phe Thr Ala Thr Gly Phe Pro Arg Val Phe Tyr
            610                 615                 620
Leu Arg Tyr His Gly Tyr Arg Lys Phe Phe Pro Leu Trp Ala Leu Ala
625                 630                 635                 640
Arg Tyr Arg Asn Leu Lys Arg Asn Asn Ala Thr Arg Val Thr Phe Gly
                645                 650                 655
Leu

<210> SEQ ID NO 10
<211> LENGTH: 620
```

```
<212> TYPE: PRT
<213> ORGANISM: Bacillus anthracis

<400> SEQUENCE: 10

Met Ser Asn Leu Leu Leu Tyr Glu Lys Ala His Glu Ile Val Arg
1               5                   10                  15

Arg Ala Thr Ala Leu Gln Thr Met Gln Trp Gln Asp Gly Thr Trp Arg
            20                  25                  30

Phe Cys Phe Glu Gly Ala Pro Leu Thr Asp Cys His Met Ile Phe Leu
        35                  40                  45

Leu Lys Leu Leu Gly Arg Asp Lys Glu Ile Glu Pro Phe Val Glu Arg
    50                  55                  60

Val Ala Ser Leu Gln Thr Asn Glu Gly Thr Trp Lys Leu His Glu Asp
65                  70                  75                  80

Glu Val Gly Gly Asn Leu Ser Ala Thr Ile Gln Ser Tyr Ala Ala Leu
                85                  90                  95

Leu Ala Ser Lys Lys Tyr Thr Lys Glu Asp Ala Asn Met Lys Arg Ala
            100                 105                 110

Glu Asn Phe Ile Gln Glu Arg Gly Gly Val Ala Arg Ala His Phe Met
        115                 120                 125

Thr Lys Phe Leu Leu Ala Ile His Gly Glu Tyr Glu Tyr Pro Ser Leu
    130                 135                 140

Phe His Leu Pro Thr Pro Ile Met Phe Leu Gln Asn Asp Ser Pro Phe
145                 150                 155                 160

Ser Ile Phe Glu Leu Ser Ser Ser Ala Arg Ile His Leu Ile Pro Met
                165                 170                 175

Met Leu Cys Leu Asn Lys Arg Phe Arg Val Gly Lys Lys Leu Leu Pro
            180                 185                 190

Asn Leu Asn His Ile Ala Gly Gly Gly Glu Trp Phe Arg Glu Asp
        195                 200                 205

Arg Ser Pro Val Phe Gln Thr Leu Leu Ser Asp Val Lys Gln Ile Ile
    210                 215                 220

Ser Tyr Pro Leu Ser Leu His His Lys Gly Tyr Glu Glu Ile Glu Arg
225                 230                 235                 240

Phe Met Lys Glu Arg Ile Asp Glu Asn Gly Thr Leu Tyr Ser Tyr Ala
                245                 250                 255

Thr Ala Ser Phe Tyr Met Ile Tyr Ala Leu Leu Ala Leu Gly His Ser
            260                 265                 270

Leu Gln Ser Ser Met Ile Gln Lys Ala Ile Ala Gly Ile Thr Ser Tyr
        275                 280                 285

Ile Trp Lys Met Glu Arg Gly Asn His Leu Gln Asn Ser Pro Ser Thr
    290                 295                 300

Val Trp Asp Thr Ala Leu Leu Ser Tyr Ala Leu Gln Glu Ala Gln Val
305                 310                 315                 320

Ser Lys Asp Asn Lys Met Ile Gln Asn Ala Thr Ala Tyr Leu Leu Lys
                325                 330                 335

Lys Gln His Thr Lys Lys Ala Asp Trp Ser Val His Ala Pro Ala Leu
            340                 345                 350

Thr Pro Gly Gly Trp Gly Phe Ser Asp Val Asn Thr Thr Ile Pro Asp
        355                 360                 365

Ile Asp Asp Thr Thr Ala Val Leu Arg Ala Leu Ala Arg Ser Arg Gly
    370                 375                 380

Asn Lys Asn Ile Asp Asn Ala Trp Lys Lys Gly Gly Asn Trp Ile Lys
385                 390                 395                 400
```

```
Gly Leu Gln Asn Asn Asp Gly Gly Trp Gly Ala Phe Glu Lys Gly Val
                405                 410                 415
Thr Ser Lys Leu Leu Ala Lys Leu Pro Ile Glu Asn Ala Ser Asp Met
            420                 425                 430
Ile Thr Asp Pro Ser Thr Pro Asp Ile Thr Gly Arg Val Leu Glu Phe
        435                 440                 445
Phe Gly Thr Tyr Ala Gln Asn Glu Leu Pro Glu Lys Gln Ile Gln Arg
    450                 455                 460
Ala Ile Asn Trp Leu Met Asn Val Gln Glu Glu Asn Gly Ser Trp Tyr
465                 470                 475                 480
Gly Lys Trp Gly Ile Cys Tyr Leu Tyr Gly Thr Trp Ala Val Met Thr
                485                 490                 495
Gly Leu Arg Ser Leu Gly Ile Pro Ser Ser Asn Pro Ser Leu Thr Arg
            500                 505                 510
Ala Ala Ser Trp Leu Glu His Ile Gln His Glu Asp Gly Gly Trp Gly
        515                 520                 525
Glu Ser Cys His Ser Ser Val Glu Lys Arg Phe Val Thr Leu Pro Phe
530                 535                 540
Ser Thr Pro Ser Gln Thr Ala Trp Ala Leu Asp Ala Leu Ile Ser Tyr
545                 550                 555                 560
Tyr Asp Thr Glu Thr Pro Ala Ile Arg Lys Gly Val Ser Tyr Leu Leu
                565                 570                 575
Ser Asn Pro Tyr Val Asn Glu Arg Tyr Pro Thr Gly Thr Gly Leu Pro
            580                 585                 590
Gly Ala Phe Tyr Ile Arg Tyr His Ser Tyr Ala His Ile Tyr Pro Leu
        595                 600                 605
Leu Thr Leu Ala His Tyr Ile Lys Lys Tyr Arg Lys
    610                 615                 620

<210> SEQ ID NO 11
<211> LENGTH: 631
<212> TYPE: PRT
<213> ORGANISM: Alicyclobacillus acidocaldarius

<400> SEQUENCE: 11

Met Ala Glu Gln Leu Val Glu Ala Pro Ala Tyr Ala Arg Thr Leu Asp
1               5                   10                  15
Arg Ala Val Glu Tyr Leu Leu Ser Cys Gln Lys Asp Glu Gly Tyr Trp
            20                  25                  30
Trp Gly Pro Leu Leu Ser Asn Val Thr Met Glu Ala Glu Tyr Val Leu
        35                  40                  45
Leu Cys His Ile Leu Asp Arg Val Asp Arg Asp Arg Met Glu Lys Ile
    50                  55                  60
Arg Arg Tyr Leu Leu His Glu Gln Arg Glu Asp Gly Thr Trp Ala Leu
65                  70                  75                  80
Tyr Pro Gly Gly Pro Pro Asp Leu Asp Thr Thr Ile Glu Ala Tyr Val
                85                  90                  95
Ala Leu Lys Tyr Ile Gly Met Ser Arg Asp Glu Glu Pro Met Gln Lys
            100                 105                 110
Ala Leu Arg Phe Ile Gln Ser Gln Gly Gly Ile Glu Ser Ser Arg Val
        115                 120                 125
Phe Thr Arg Met Trp Leu Ala Leu Val Gly Glu Tyr Pro Trp Glu Lys
    130                 135                 140
Val Pro Met Val Pro Pro Glu Ile Met Phe Leu Gly Lys Arg Met Pro
```

-continued

```
            145                 150                 155                 160
Leu Asn Ile Tyr Glu Phe Gly Ser Trp Ala Arg Ala Thr Val Val Ala
                    165                 170                 175
Leu Ser Ile Val Met Ser Arg Gln Pro Val Phe Pro Leu Pro Glu Arg
                180                 185                 190
Ala Arg Val Pro Glu Leu Tyr Glu Thr Asp Val Pro Pro Arg Arg Arg
            195                 200                 205
Gly Ala Lys Gly Gly Gly Trp Ile Phe Asp Ala Leu Asp Arg Ala
        210                 215                 220
Leu His Gly Tyr Gln Lys Leu Ser Val His Pro Phe Arg Arg Ala Ala
225                 230                 235                 240
Glu Ile Arg Ala Leu Asp Trp Leu Leu Glu Arg Gln Ala Gly Asp Gly
                245                 250                 255
Ser Trp Gly Gly Ile Gln Pro Pro Trp Phe Tyr Ala Leu Ile Ala Leu
            260                 265                 270
Lys Ile Leu Asp Met Thr Gln His Pro Ala Phe Ile Lys Gly Trp Glu
        275                 280                 285
Gly Leu Glu Leu Tyr Gly Val Glu Leu Asp Tyr Gly Gly Trp Met Phe
    290                 295                 300
Gln Ala Ser Ile Ser Pro Val Trp Asp Thr Gly Leu Ala Val Leu Ala
305                 310                 315                 320
Leu Arg Ala Ala Gly Leu Pro Ala Asp His Asp Arg Leu Val Lys Ala
                325                 330                 335
Gly Glu Trp Leu Leu Asp Arg Gln Ile Thr Val Pro Gly Asp Trp Ala
            340                 345                 350
Val Lys Arg Pro Asn Leu Lys Pro Gly Gly Phe Ala Phe Gln Phe Asp
        355                 360                 365
Asn Val Tyr Tyr Pro Asp Val Asp Asp Thr Ala Val Val Val Trp Ala
    370                 375                 380
Leu Asn Thr Leu Arg Leu Pro Asp Glu Arg Arg Arg Arg Asp Ala Met
385                 390                 395                 400
Thr Lys Gly Phe Arg Trp Ile Val Gly Met Gln Ser Ser Asn Gly Gly
                405                 410                 415
Trp Gly Ala Tyr Asp Val Asp Asn Thr Ser Asp Leu Pro Asn His Ile
            420                 425                 430
Pro Phe Cys Asp Phe Gly Glu Val Thr Asp Pro Pro Ser Glu Asp Val
        435                 440                 445
Thr Ala His Val Leu Glu Cys Phe Gly Ser Phe Gly Tyr Asp Asp Ala
    450                 455                 460
Trp Lys Val Ile Arg Arg Ala Val Glu Tyr Leu Lys Arg Glu Gln Lys
465                 470                 475                 480
Pro Asp Gly Ser Trp Phe Gly Arg Trp Gly Val Asn Tyr Leu Tyr Gly
                485                 490                 495
Thr Gly Ala Val Val Ser Ala Leu Lys Ala Val Gly Ile Asp Thr Arg
            500                 505                 510
Glu Pro Tyr Ile Gln Lys Ala Leu Asp Trp Val Glu Gln His Gln Asn
        515                 520                 525
Pro Asp Gly Gly Trp Gly Glu Asp Cys Arg Ser Tyr Glu Asp Pro Ala
    530                 535                 540
Tyr Ala Gly Lys Gly Ala Ser Thr Pro Ser Gln Thr Ala Trp Ala Leu
545                 550                 555                 560
Met Ala Leu Ile Ala Gly Gly Arg Ala Glu Ser Glu Ala Ala Arg Arg
                565                 570                 575
```

```
Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
            595                 600                 605

Tyr Thr Met Tyr Arg His Val Phe Pro Thr Leu Ala Leu Gly Arg Tyr
            610                 615                 620

Lys Gln Ala Ile Glu Arg Arg
625                 630
```

SQUALENE HOPENE CYCLASE AND USE THEREOF FOR PRODUCING AMBROXAN

INTRODUCTION

This application is a U.S. National Stage Application of PCT/US2018/019633 filed Feb. 26, 2018 and claims benefit of priority to U.S. Provisional Application Ser. No. 62/463,163 filed Feb. 24, 2017, the contents of each of which are incorporated herein by reference in their entirety.

BACKGROUND

Compounds with the dodecahydronaphtho[2,1-b]furan skeleton are of great economic importance as aroma chemicals. Among these, (3aR,5aS,9aS,9bR)-dodecahydro-3a,6,6,9a-tetramethylnaphtho [2,1-b]furan), known as ambroxan, is of particular importance for providing base notes of perfume compositions. Originally obtained from sperm whales' ambergris, synthetic methods have been developed for the production of ambroxan. In one approach, sclareol, a constituent of clary sage (*Salvia sclarea*), is used as a starting material. Oxidative degradation of sclareol with, e.g., chromic acid, permanganate, $H_2O_2$ or ozone provides sclareolid, which is subsequently reduced, e.g., using $LiAlH_4$ or $NaBH_4$ to give ambrox-1,4-diol. Alternatively, sclareolid can be prepared from sclareol by means of a biotransformation using *Hyphozyma roseoniger* (EP 0204009). Finally, ambrox-1,4-diol is cyclized in a series of chemical processes to give compound ambroxan ((−)-2). The preparation of the racemate of ambroxan, rac-2, has been accomplished, inter alia, via homofarnesylic acid and 4-(2,6,6-trimethylcyclohex-1-enyl)butan-2-one.

In another approach, ambroxan is biocatalytically prepared using squalene hopene cyclase (SHC; Scheme 1) (Neumann, et al. (1986) *Biol. Chem. Hoppe Seyler* 367:723).

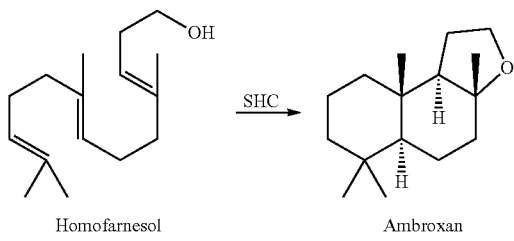

Scheme 1

While SHC naturally catalyzes the cyclization of squalene to hopane, catalysis of ambroxan is a secondary reaction with a specific activity of 0.02 mU/mg protein. SHC from *Alicyclobacillus acidocaldarius* (formerly *Bacillus acidocaldarius*), *Zymomonas mobilis* and *Bradyrhizobium japonicum* have been purified and characterized in terms of their natural (e.g., squalene) and non-natural substrates (e.g., homofarnesol and citral). See, for example, WO 2010/139719, WO 2012/066059, JP 2009060799, and Seitz, et al. (2012) *J. Molecular Catalysis B: Enzymatic* 84:72-77). In addition, WO 2016/170099 describes SHC mutants with improved rates of conversion of E,E-homofarnesol to ambroxan have been described.

SUMMARY OF THE INVENTION

This invention provides a recombinant vector harboring a nucleic acid molecule encoding Squalene Hopene Cyclase (GHC), the amino acid sequence of which is SEQ ID NO:2 or an amino acid sequence having at least 90% sequence identity with SEQ ID NO:2. In some embodiments, the SHC has an amino acid substitution, relative to SEQ ID NO:2, at position 45, 46, 54, 86, 139, 142, 178, 184, 194, 239, 278, 326, 335, 386, 455, 460, 603, 623, 624, 656, 658 or a combination thereof. A recombinant host cell harboring the recombinant vector is also provided as is a method for producing ambroxan by providing homofarnesol to a recombinant host cell that expresses SHC, the amino acid sequence of which is SEQ ID NO:2 or an amino acid sequence having at least 90% sequence identity with SEQ ID NO:2 and collecting ambroxan produced by the SHC. In accordance with some embodiments of the method, the homofarnesol is provided in the presence of a solubilizing agent, e.g., a nonionic surfactant. In accordance with other embodiments of the method, the homofarnesol includes (3E,7E) homofarnesol. This invention further provides a recombinant SHC polypeptide having at least 90% sequence identity to SEQ ID NO:2 and including an amino acid substitution, relative to SEQ ID NO:2, at position 45, 46, 54, 86, 139, 142, 178, 184, 194, 239, 278, 326, 335, 386, 455, 460, 603, 623, 624, 656, 658 or a combination thereof.

BRIEF DESCRIPTION OF THE DRAWINGS

FIG. 1A to FIG. 1C provide an amino acid sequence comparison of *Gluconobacter morbifer* Squalene Hopene Cyclase (GmSHC) with SHC enzymes from *Z. mobilis* (ZmSHC), *Bradyrhizobium* sp. (BspSHC), *Rhodopseudomonas palustris* (RpSHC), *Streptomyces coelicolor* (ScSHC), *Burkholderia ambifaria* (BamSHC), *Bacillus anthracis* (BanSHC) and *A. acidocaldarius* (AaSHC). Underlined residues represent the core sequence Gln-Xaa-Xaa-Xaa-Gly-Xaa-Trp (SEQ ID NO:3) and bolded residues represent the Asp-Xaa-Asp-Asp-Thr-Ala (SEQ ID NO:4) active site motif.

DETAILED DESCRIPTION OF THE INVENTION

Figure 2:
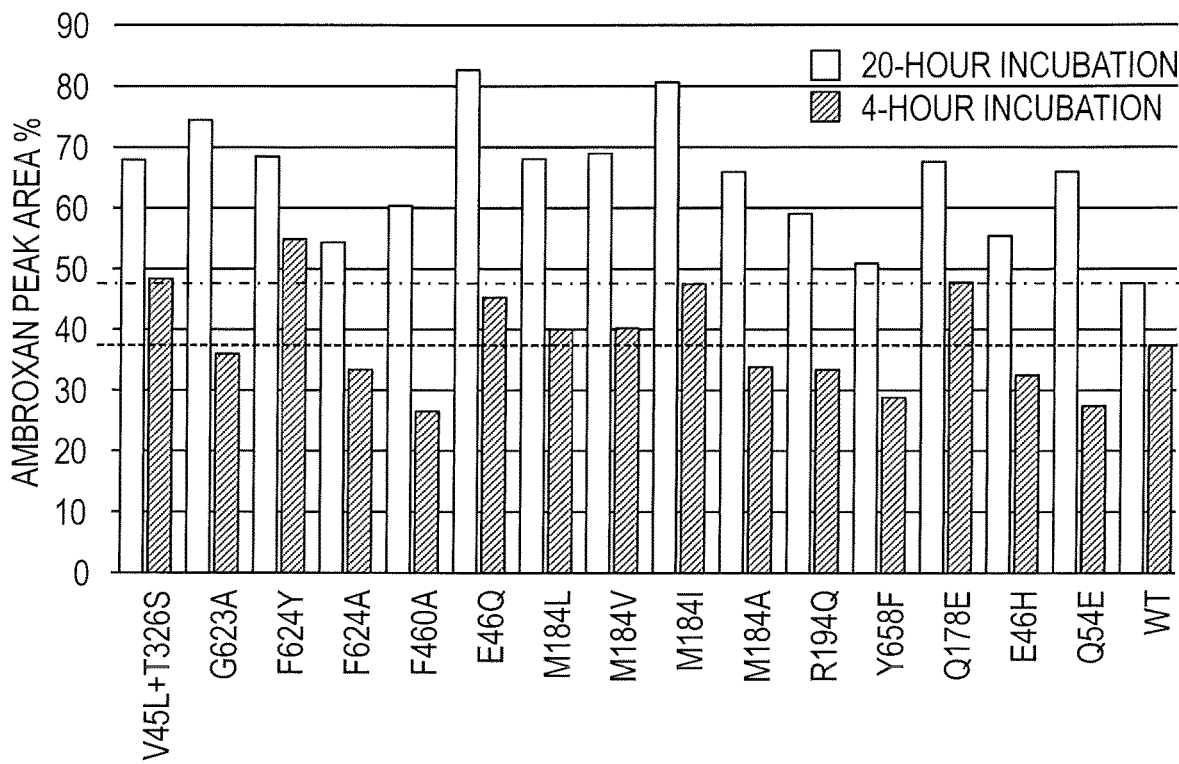
FIG. 2 shows the % peak area of ambroxan produced by mutant GmSHC enzymes following incubation at 37° C. for 6 and 20 hours with 15 mg/mL homofarnesol. Dashed line shows the production of ambroxan by wild-type SHC.

This invention provides a Squalene Hopene Cyclase (SHC), or more preferably a homofarnesol-ambroxan cyclase (HAC), isolated from *Gluconobacter morbifer* and method for using the *G. morbifer* SHC (GmSHC) to biocatalytically convert homofarnesol to ambroxan. The nucleotide sequence of GmSHC is provided in SEQ ID NO:1. The amino acid sequence of GmSHC (SEQ ID NO:2) is available under GENBANK Accession Nos. WP_040507485 and EHH69691. An alignment of the GmSHC amino acid sequence with SHC amino acid sequences from *Z. mobilis*, *Bradyrhizobium* sp., *R. palustris*, *S. coelicolor*, *B. ambifaria*, *B. anthracis* and *A. acidocaldarius* (FIG. 1A to FIG. 1C) indicates amino acid sequence identities ranging between 37% and 76% (Table 1).

TABLE 1

| Source organism | Accession No. | GmSHC Identity |
|---|---|---|
| Z. mobilis | Q5NM88 | 76% |
| Bradyrhizobium sp. | A5EBP6 | 72% |
| B. ambifaria | Q0B5S3 | 37% |
| B. anthracis | A0A0E0W268 | 48% |
| R. palustris | WP_011665849 | 66% |
| S. coelicolor | Q9X7V9 | 45% |
| A. acidocaldarius | P33247 | 44% |

GmSHC contains the core sequence Gln-Xaa-Xaa-Xaa-Gly-Xaa-Trp (SEQ ID NO:3)(Reipen, et al. (1995) Microbiology 141:155-161), as well as the Asp-Xaa-Asp-Asp-Thr-Ala (SEQ ID NO:4) motif, which correlates with the SHC active site (Wendt, et al. (1997) Science 277:1811-5). See FIG. 1A to FIG. 1C. The data presented herein demonstrate that the GmSHC enzyme, when expressed in a heterologous host cell, e.g., E. coli, can readily convert homofarnesol to ambroxan. Therefore, the GmSHC enzyme, as well as derivatives thereof, are of use in a method for preparing ambroxan using homofarnesol as a feedstock or starting material.

As used herein, the term "ambroxan" refers to (3aR,5aS,9aS,9bR)-dodecahydro-3a,6,6,9a-tetramethylnaphtho [2,1-b]furan), which is known commercially as AMBROX (Firmenich), Ambroxan (Henkel) AMBROFIX (Givaudan), AMBERLYN (Quest), CETALOX Laevo (Firmenich), AMBERMOR (Aromor) and/or Norambrenolide Ether (Pacific). The desirable sensory benefits of ambroxan come from the (−) stereoisomer rather than the (+) enantiomer. The odor of the (−) stereoisomer is described as musk-like, woody, warm or ambery whereas the (+) enantiomer has a relatively weak odor note. Thus, materials enriched with (−)-ambroxan are one feature of this invention.

As described herein, (−)-ambroxan can be synthesized from homofarnesol (Scheme 1). There are four known isomers of homofarnesol, the (3Z,7Z, i.e., ZZ), (3E,7Z, i.e., EZ), (3Z,7E, i.e., ZE) and (3E,7E, i.e., EE) isomers. According to Neumann, et al. ((1986) Biol. Chem. Hoppe Seyler 367:723), (−)-ambroxan is primarily obtained from EE homofarnesol. US 2012/0135477 indicates that the Z. mobilis SHC enzyme can convert ZE homofarnesol to (−)-ambroxan. However, Schaefer ((2011) Chemie Unserer Zeit 45:374-388) indicates that ZE homofarnesol is only converted to 9b-epi-ambroxan and not to (−)-ambroxan. Accordingly, the homofarnesol feedstock/starting material of this invention is a single isomer or is a mixture of two or more isomers of homofarnesol. In some embodiments, the homofarnesol starting material is a mixture of the four isomers EE:EZ:ZZ:ZE. In other embodiments, the homofarnesol starting material is a mixture of ZE:EE, ZE:EZ or EE:EZ. In embodiments including the use of a mixture of EE:EZ, preferably the weight ratio of EE:EZ is in the range of 99:1 to about 50:50. More particularly, the homofarnesol starting material has an EE:EZ weight ratio of 80:20 or 70:30. In particular embodiments, the homofarnesol starting material has >90 (3E,7E) homofarnesol. An exemplary EE:EZ stereoisomeric mixture of homofarnesol has the CAS number of 35826-67-6.

Preferably, the starting material used in the preparation of (−)-ambroxan is stereoisomerically pure (3E,7E) homofarnesol (EEH). Methods for preparing EEH are known in the art and described, e.g., by Dodd, et al. (1992) J. Org. Chem. 57:2794; Barrero, et al. (1996) J. Org. Chem. 61:2215; Kocienski et al. (1989) J. Org. Chem. 54:1215; WO 92/06063 and U.S. Pat. No. 9,493,385.

As used herein, "GmSHC" refers to the Squalene Hopene Cyclase isolated from Gluconobacter morbifer. In particular, when not modified by "mutant" or "derivative," "GmSHC" refers to a wild-type protein having the amino acid sequence according to SEQ ID NO:2. By comparison, "mutant GmSHC," "GmSHC mutant," or "GmSHC derivative" refers to a modified or variant amino acid sequence which is altered compared to the amino acid sequence of the reference (or wild-type) GmSHC sequence according to SEQ ID NO:2. In one embodiment, a GmSHC derivative has at least one alteration that modifies (e.g., increases) the activity of the enzyme for its substrate (e.g., homofarnesol, in particular EEH). In another embodiment, a GmSHC derivative has at least one alteration that modifies the stability, localization, or expression of the enzyme in a heterologous host cell.

As used herein, the term "amino acid alteration" means an insertion of one or more amino acid residues, a deletion of one or more amino acid residues or a substitution (which may be conservative or non-conservative) of one or more amino acid residues with one or more different amino acids relative to the amino acid sequence of a reference amino acid sequence (such as, for example, the wild-type amino acid sequence of SEQ ID NO:2). The amino acid alteration can be easily identified by a comparison of the amino acid sequences of the GmSHC derivative amino acid sequence with the amino acid sequence of the reference GmSHC.

Conservative amino acid substitutions may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic—Met, Ala, Val, Leu, Ile; (2) neutral hydrophilic—Cys, Ser, Thr, Asn, Gln; (3) acidic—Asp, Glu; (4) basic—His, Lys, Arg; (5) residues that influence chain orientation—Gly, Pro; and (6) aromatic: Trp, Tyr, Phe. Accordingly, as used herein, the term "conservative substitutions" means an exchange of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt alpha-helices. Some preferred conservative substitutions within the above six groups are exchanges within the following sub-groups: (i) Ala, Val, Leu and Ile; (ii) Ser and Thr; (iii) Asn and Gln; (iv) Lys and Arg; and (v) Tyr and Phe. Given the known genetic code, and recombinant and synthetic DNA techniques, the skilled scientist readily can construct DNAs encoding the conservative amino acid variants.

As used herein, "non-conservative substitutions" or "non-conservative amino acid exchanges" are defined as exchanges of an amino acid by another amino acid listed in a different group of the six standard amino acid groups (1) to (6) as shown above. Typically, the GmSHC derivatives of the present disclosure are prepared using non-conservative substitutions that alter the biological function of the wild-type GmSHC.

In various embodiments, the amino acid alteration or combination of amino acid alterations enhances the activity of the GmSHC derivative for converting homofarnesol to ambroxan compared to wild-type GmSHC, which does not have the amino acid alteration or combination of amino acid alterations. Protein modeling may be used to guide such substitutions, deletions, or insertions in the GmSHC reference sequence. For example, a structural model of the GmSHC amino acid sequence may be created using the coordinates for the *A. acidocaldarius* SHC. Such a homology model is useful for directing improvement of GmSHC enzyme for converting homofarnesol to ambroxan, such as a higher production of ambroxan upon contact with a homofarnesol substrate than the reference wild-type enzyme.

Amino acid alterations such as amino acid substitutions may be introduced using known protocols of recombinant gene technology including PCR, gene cloning, site-directed mutagenesis of cDNA, transfection of host cells, and in vitro transcription, which may be used to introduce such changes to the GmSHC sequence resulting in a GmSHC derivative enzyme. The derivatives can then be screened for GmSHC functional activity.

The GmSHC derivative may have from about 1 to about 45 amino acid alterations, about 1 to about 40 amino acid alterations, about 1 to about 35 amino acid alterations, about 1 to about 30 amino acid alterations, about 1 to about 25 amino acid alterations, from about 1 to about 20 amino acid alterations, about 1 to about 15 amino acid alterations, about 1 to about 10 amino acid alterations, or from about 1 to about 5 amino acid alterations relative to the amino acid sequence of the reference (or wild-type) GmSHC sequence according to SEQ ID NO:2.

Alternatively, the GmSHC derivative can have at least 5 or at least 10 amino acid alterations relative to the amino acid sequence of the reference (or wild-type) GmSHC sequence according to SEQ ID NO:2, but not more than about 20 or 30 amino acid alterations. In various embodiments, the GmSHC derivative may have about 1 amino acid alteration, about 2 amino acid alterations, about 3 amino acid alterations, about 4 amino acid alterations, about 5 amino acid alterations, about 6 amino acid alterations, about 7 amino acid alterations, about 8 amino acid alterations, about 9 amino acid alterations, about 10 amino acid alterations, about 15 amino acid alterations, about 20 amino acid alterations, about 25 amino acid alterations, about 30 amino acid alterations, about 35 amino acid alterations, about 40 amino acid alterations, about 45 amino acid alterations, or about 50 amino acid alterations relative to the reference GmSHC.

In these or other embodiments, the GmSHC derivative shares at least about 50% sequence identity, at least about 55% sequence identity, at least about 60% sequence identity, at least about 65% sequence identity, at least about 70% sequence identity, at least about 75% sequence identity, at least about 80% sequence identity, at least about 85% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to reference GmSHC (SEQ ID NO:2).

In some embodiments, a GmSHC derivative includes amino acid alterations at one or more of positions 45, 46, 54, 86, 139, 142, 178, 184, 194, 239, 278, 326, 335, 386, 455, 460, 603, 623, 624, 656 or 658 relative to SEQ ID NO:2. In some embodiments, a GmSHC derivative has one or more of the following amino acid substitutions: V45X, E46X, Q54X, S86X, F139X, Y142X, Q178X, M184X, R194X, G239X, I278X, T326X, L335X, E386X, I455X, F460X, Q603X, G623X, F624X, L656X or Y658X relative to SEQ ID NO:2, wherein:

X in V45X is A, C, D, E, F, G, H, I, K, L, M, N, P, Q, R, S, T, W or Y;

X in E46X is A, C, D, F, G, H, I, K, L, M, N, P, Q, R, S, T, V, W or Y;

X in O54X is A, C, D, E, F, G, H, I, K, L, M, N, P, R, S, T, V, W or Y;

X in S86X is A, C, D, E, F, G, H, I, K, L, M, N, P, Q, R, T, V, W or Y;

X in F139X is A, C, D, E, G, H, I, K, L, M, N, P, Q, R, S, T, V, W or Y;

X in Y142X is A, C, D, E, F, G, H, I, K, L, M, N, P, Q, R, S T, V or W;

X in Q178X is A, C, D, E, F, G, H, I, K, L, M, N, P, R, S, T, V, W or Y;

X in M184X is A, C, D, E, F, G, H, I, K, L, N, P, Q, R, S, T, V, W or Y;

X in R194X is A, C, D, E, F, G, H, I, K, L, M, N, P, Q, S, T, V, W or Y;

X in G239X is A, C, D, E, F, H, I, K, L, M, N, P, Q, R, S, T, V, W or Y;

X in I278X is A, C, D, E, F, G, H, K, L, M, N, P, Q, R, S, T, V, W or Y;

X in T326X is A, C, D, E, F, G, H, I, K, L, M, N, P, Q, R, S, V, W or Y;

X in L335X is A, C, D, E, F, G, H, I, K, M, N, P, Q, R, S, T, V, W or Y;

X in E386X is A, C, D, F, G, H, I, K, L, M, N, P, Q, R, S, T, V, W or Y;

X in I455X is A, C, D, E, F, G, H, K, L, M, N, P, Q, R, S, T, V, W or Y;

X in F460X is A, C, D, E, G, H, I, K, L, M, N, P, Q, R, S, T, V, W or Y;

X in Q603X is A, C, D, E, F, G, H, I, K, L, M, N, P, R, S, T, V, W or Y;

X in G623X is A, C, D, E, F, H, I, K, L, M, N, P, Q, R, S, T, V, W or Y;

X in F624X is A, C, D, E, G, H, I, K, L, M, N, P, Q, R, S, T, V, W or Y;

X is L656X is A, C, D, E, F, G, H, I, K, M, N, P, Q, R, S, T, V, W or Y; and

X is Y658X is A, C, D, E, F, G, H, I, K, L, M, N, P, Q, R, S, T, V, or W.

In certain embodiments, the GmSHC derivative has one or a combination of the following amino acid substitutions V45I, V45Q, V45L, E46H, E46Q, Q54E, S86A, F139L, Y142R, Q178E, M184A, M184L, M184I, M184V, R194Q, G239V, I278V, T326S, L335F, E386Q, I455T, F460A, Q603H, G623A, G623V, F624Y, F624A, L656E and Y658F relative to SEQ ID NO:2. In other embodiments, the GmSHC derivative has a combination of substitutions relative to SEQ ID NO:2 as set out in Table 2, or any combination thereof.

TABLE 2

| Combination | Mutations | No. of Mutations |
| --- | --- | --- |
| A | Y142R + I455T | 2 |
| B | S86A + F139L | 2 |
| C | Q603H + F624Y | 2 |
| D | V45L + T326S | 2 |
| E | F139L + F624Y | 2 |
| F | E46Q + M184I | 2 |
| G | E46Q + M184A | 2 |
| H | E46Q + M184V | 2 |
| I | M184I + Q178E | 2 |
| J | E46Q + F624Y | 2 |
| K | Q54E + M184I | 2 |
| L | M184V + Q178E | 2 |
| M | E46Q + G623A | 2 |

TABLE 2-continued

| Combination | Mutations | No. of Mutations |
|---|---|---|
| N | E46Q + M184L | 2 |
| O | Q54E + R194Q | 2 |
| P | Q54E + E46Q | 2 |
| Q | F139L + Y142R + I455T | 3 |
| R | Y142R + I455T + F624Y | 3 |
| S | Y142R + I455T + G239V | 3 |
| T | E46Q + M184I + G623A | 3 |
| U | E46Q + M184I + F624Y | 3 |
| V | E46Q + M184I + R194Q | 3 |
| W | Q54E + M184I + F624Y | 3 |
| X | E46Q + M184I + F624Y + G623A | 4 |
| Y | E46Q + M184I + V45L + T326S | 4 |
| Z | F139L + Y142R + I455T + F624Y | 4 |
| AA | E46Q + M184I + F624Y + R194Q | 4 |
| BB | Q54E + M184I + V45L + T326S | 4 |
| CC | Q54E + M184I + F624Y + T326S | 4 |
| DD | Q54E + E46Q + M184I + F624Y | 4 |
| EE | Q54E + R194Q + V45L + T326S | 4 |
| FF | Q54E + E46Q + M184I + V45L + T326S | 5 |
| GG | Q54E + M184I + V45L + T326S + F624Y | 5 |
| HH | E46Q + M184I + F624Y + R194Q + V45L + T326S | 6 |
| II | E46Q + M184I + F624Y + G623A + V45L + T326S | 6 |
| JJ | E46Q + M184I + F624Y + R194Q + V45L + T326S | 6 |
| KK | E46Q + M184I + F624Y + R194Q + V45L + T326S + G623A | 7 |

Amino acid substitutions in *A. acidocaldarius* SHC (AacSHC) at amino acid positions corresponding to F139L, Y142, I455, G239 and F624 of GmSHC have been shown to increase the activity of the AacSHC enzyme in terms of EEH conversion to ambroxan. See WO 2016/170099. Further, F601 of AacSHC has been identified as a highly conserved amino acid residue among the prokaryotic and eukaryotic SHC species. It has been reported that AacSHC derivative F601Y shows a greatly increased Vmax for an oxidosqualene substrate (not squalene); however, F601Y shows a decrease in affinity (i.e., a higher $K_M$) and a decrease in catalytic efficiency/activity ($Kcat/K_M$) relative to the wild-type AacSHC when squalene is used. See Hoshino & Sato (2002) *Chem. Commun.* (4):291-301. Notably, the SHC derivative equivalent to F601Y in GmSHC is F624Y.

Accordingly, in certain embodiments of this invention, the GmSHC derivative has at least the substitution Q54E, F624Y or Y142R in combination with at least one or more of V45I, V45Q, V45L, E46H, E46Q, S86A, F139L, Q178E, M184A, M184L, M184I, M184V, R194Q, G239V, I278V, T326S, L335F, E386Q, I455T, F460A, Q603H, G623A, G623V, L656E and Y658F relative to SEQ ID NO:2. In particular embodiments, the GmSHC derivative has a combination of mutations listed in Table 2. In some embodiments, the GmSHC derivative is a modified GmSHC polypeptide having an amino acid sequence that has up to 4 mutations compared to the wild-type/reference amino acid sequence according to SEQ ID NO:2 and includes at least the substitution Q54E, F624Y or Y142R relative to SEQ ID NO:2.

Assays for determining and quantifying SHC activity are described herein and are known in the art. By way of illustration, GmSHC and/or GmSHC derivative activity can be determined by incubating purified GmSHC enzyme or extracts from host cells or a complete recombinant host organism that has produced the GmSHC enzyme with an appropriate substrate under appropriate conditions and carrying out an analysis of the reaction products (e.g., by gas chromatography (GC) or HPLC analysis). Further details on GmSHC enzyme activity assays and analysis of the reaction products are provided in the Examples. These assays include producing the GmSHC in recombinant host cells (e.g., *E. coli*).

As used herein, the term "activity" means the ability of an enzyme to react with a substrate to provide a target product. The activity can be determined in what is known as an activity test via the increase of the target product, the decrease of the substrate (or starting materials) or via a combination of these parameters as a function of time. The GmSHC of the present disclosure is characterized by its ability to bioconvert homofarnesol into ambroxan.

In embodiments directed to the use of a GmSHC derivative, preferably the GmSHC derivative exhibits a better target yield than the reference GmSHC protein. The term "target yield" refers to the gram of recoverable product per gram of feedstock (which can be calculated as a percent molar conversion rate). In addition, a GmSHC derivative can exhibit a modified (e.g., increased) target productivity relative to the reference GmSHC protein. The term "target productivity" refers to the amount of recoverable target product in grams per liter of fermentation capacity per hour of bioconversion time (i.e., time after the substrate was added). Moreover, a GmSHC derivative can exhibit a modified target yield factor compared to the reference GmSHC protein. The term "target yield factor" refers to the ratio between the product concentration obtained and the concentration of the GmSHC derivative (for example, purified GmSHC enzyme or an extract from the recombinant host cells expressing the GmSHC enzyme) in the reaction medium. In certain embodiments, a GmSHC derivative exhibits at least a 2-, 3-, 4-, 6-, 8-, 10-, 12-, 14-, 16-, 18-, 20-, 25-, 30-, 35-, 40-, 45-, 50-, 55-, 60-, 65-, 70-, 75-, 80-, 85-, 90-, 95-, or 100-fold increase in enzymatic activity (e.g., conversion of homofarnesol to ambroxan) relative to the reference GmSHC protein (e.g., SEQ ID NO:2).

A functional homolog of the GmSHC proteins disclosed herein is also included within the scope of this invention. A "functional homolog" is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild-type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Techniques for obtaining functional homologs of the GmSHC enzyme described herein are known and include, inter alia, directed evolution techniques, site-directed mutagenesis techniques and random mutagenesis techniques, which can be used to increase specific activity of the GmSHC enzyme, alter substrate specificity, alter expression levels, or alter subcellular location in a desired manner.

Desirably the GmSHC enzyme and functional homolog share at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity. Preferably, the functional homolog and the reference polypeptide exhibit the indicated sequence identity over a continuous stretch of 20, 30, 40, 45, 50, 60, 70, 80, 90, 100 or more amino acid residues.

To facilitate GmSHC expression and ambroxan production and isolation, the GmSHC or GmSHC derivative is expressed in a recombinant host cell. The term "recombinant host," also referred to as a "genetically modified host cell" or "transgenic cell" denotes a host cell that includes a heterologous nucleic acid or the genome of which has been augmented by at least one incorporated DNA sequence. A host cell of the present disclosure may be genetically engineered with a nucleic acid molecule or vector containing a nucleic acid molecule encoding a GmSHC or GmSHC derivative.

The term "nucleic acid molecule," as used herein, refers to polynucleotides of the disclosure which can be DNA, cDNA, genomic DNA, synthetic DNA, or RNA, and can be double-stranded or single-stranded, the sense and/or an antisense strand. The term "nucleic acid molecule" shall particularly apply to the polynucleotide(s) as used herein (e.g., as full-length nucleotide sequence or fragments or parts thereof), which encodes a GmSHC or GmSHC derivative, e.g., SEQ ID NO:1. The term also includes a cDNA; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; and a DNA encoding a non-naturally occurring protein such as a fusion protein. Fusion proteins can add one or more amino acids to a protein (e.g., a His-tag), usually at the N-terminus of the protein but also at the C-terminus or fused within regions of the protein. Such fusion proteins or fusion vectors encoding such proteins typically provide (i) an increase in the production of recombinant proteins; (ii) an increase in the solubility of the recombinant protein; and/or (iii) an aid in the purification of the recombinant protein by providing a ligand for affinity purification. In certain embodiments, the GmSHC or GmSHC derivative includes a leader sequence to support the expression and/or activity of the GmSHC or GmSHC derivative in a recombinant host cell, e.g., E. coli.

The term "nucleic acid molecule" also includes codon optimized sequences suitable for expression in a particular recombinant host cell (e.g., E. coli host cell). The term "codon optimized" means a protein coding sequence which has been adapted for expression in a prokaryotic or a eukaryotic host cell, particularly bacterial host cells such as E. coli host cells by substitution of one or more or preferably a significant number of codons with codons that are more frequently used in bacterial host cell genes. In this regard, the nucleotide sequence encoding the reference sequence SEQ ID NO:1 and all variants/derivatives thereof may be the original one as found in the source (e.g., GmSHC) or the nucleotide sequence can be codon-optimized for the selected host organisms, such as e.g., E. coli.

The term "isolated DNA," as used herein, refers to nucleic acids or polynucleotides isolated from a natural source (e.g., Gluconobacter morbifer) or nucleic acids or polynucleotides produced by recombinant DNA techniques, e.g., a DNA construct include a polynucleotide heterologous to a host cell, which is optionally incorporated into the host cell. A chimeric nucleotide sequence may specifically be produced as a recombinant molecule. The term "recombinant," with respect to enzymes, refers to enzymes produced by recombinant DNA techniques, i.e., produced from cells transformed by an exogenous DNA construct encoding the desired enzyme. The term "recombinant" shall specifically apply to assembly of polynucleotides, joining together such polynucleotides or parts thereof, with or without recombination to achieve a cross-over or a gene mosaic. For example, it is performed to join together nucleic acid segments of desired functions to generate a desired combination of functions. A recombinant nucleic acid molecule encoding a polypeptide described herein includes the coding sequence for that polypeptide operably linked, in sense orientation, to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired.

A coding sequence and a regulatory region are considered to be operably linked when the regulatory region and coding sequence are positioned so that the regulatory region is effective for regulating transcription or translation of the sequence. Transcriptional/translational regulatory elements include, but are not limited to, inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include, but are not limited to, regulatory elements such as the CUP-1 promoter; the tet-repressor as employed, for example, in the tet-on or tet-off systems; the lac system, and the trp system regulatory elements. By way of example, Isopropyl β-D-1-thiogalactopyranoside (IPTG) is an effective inducer of gene expression in the concentration range of 100 µM to 1.0 mM. This compound is a molecular mimic of allolactose, a lactose metabolite that triggers transcription of the lac operon, and it is therefore used to induce gene expression when the gene is under the control of the lac operator. Another example of a regulatory element which induces gene expression is lactose.

The nucleic acid molecule(s) of the present disclosure can also form part of a hybrid gene encoding additional polypeptide sequences, for example, a sequence that functions as a marker or reporter. Examples of marker and reporter genes including beta-lactamase, chloramphenicol acetyltransferase (CAT), adenosine deaminase (ADA), aminoglycoside phosphotransferase dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). As with many of the standard procedures associated with the practice of the disclosure, skilled artisans will be aware of additional useful reagents, for example, additional sequences that can serve the function of a marker or reporter.

In some embodiments, the present disclosure provides a recombinant nucleic acid molecule encoding wild-type GmSHC or a GmSHC derivative described above, which may be inserted into a vector for expression and optional purification. Such vectors are referred to herein as "expression vectors." Usually expression vectors suitable for DNA recombination techniques are typically of the plasmid type. An expression vector includes a recombinant nucleic acid molecule encoding wild-type GmSHC or a GmSHC derivative as described herein and the necessary regulatory regions suitable for expressing the polypeptide. Such vectors include nucleic acid molecules that are not naturally present in the host cell, nucleic acid molecules that are not normally transcribed into RNA or translated into a protein ("expressed") and other genes or nucleic acid molecules which one desires to introduce into the host cell. It will be appreciated that typically the genome of a recombinant host cell described herein is augmented through the stable introduction of one or more recombinant nucleic acid molecules. However, autonomous or replicative plasmids or vectors can also be used within the scope of this disclosure. Moreover, the present disclosure can be practiced using a low copy number, e.g., a single copy, or high copy number plasmid or vector. In certain embodiments, the vector of the present disclosure is a plasmid, phagemid, phage, cosmid, artificial bacterial or artificial yeast chromosome, knock-out or knock-in construct, synthetic nucleic acid molecule or cassette produced in the form of a linear polynucleotide, plasmid, megaplasmid, synthetic or artificial chromosome, such as plant, bacterial, mammalian or yeast artificial chromosome.

According to this invention, the GmSHC or a GmSHC derivative encoded by the recombinant nucleic acid molecule is constitutively or inducibly expressed within the cell upon introduction of the vector. Microbial cells are transformed with a vector encoding the GmSHC or a GmSHC derivative using standard transforming techniques. In a suitable embodiment, DNA providing an origin of replication is included in the vector. The origin of replication may be suitably selected by the skilled person. Depending on the nature of the genes, a supplemental origin of replication may not be required if sequences are already present with the genes or genome that are operable as origins of replication themselves.

With the context of the present invention, a microbial cell (e.g., a bacterial or yeast cell) is transformed, when an exogenous or heterologous DNA has been introduced inside the cell. The transforming DNA may or may not be integrated, i.e., covalently linked into the genome of the cell. In prokaryotes, and yeast, for example, the transforming DNA may be maintained on an episomal element such as a plasmid. With respect to eukaryotic cells, a stably transfected cell is one in which the transfected DNA has become integrated into a chromosome so that it is inherited by daughter cells through chromosome replication. This stability is demonstrated by the ability of the eukaryotic cell to establish cell lines or clones including of a population of daughter cells containing the transforming DNA.

Host cells that may be used for purposes of the disclosure include, but are not limited to, prokaryotic cells such as bacteria (e.g., *E. coli* and *B. subtilis*), which can be transformed with, for example, recombinant bacteriophage DNA, plasmid DNA, bacterial artificial chromosome, or cosmid DNA expression vectors containing the GmSHC nucleic acid molecules of the disclosure; simple eukaryotic cells like yeast (for example, *Saccharomyces* and *Pichia*), which can be transformed with, for example, recombinant yeast expression vectors containing the polynucleotide molecule of the disclosure; insect cells (e.g., a baculovirus insect cell expression system); human cells (e.g., HeLa, CHO and Jurkat), and plant cells (*Arabidopsis* and tobacco). Depending on the host cell and the respective vector used to introduce the nucleic acid molecule of the disclosure, the nucleic acid molecule can integrate, for example, into the chromosome or the mitochondrial DNA or can be maintained extrachromosomally, for example, episomally, or can be only transiently harbored by the cell.

In embodiments pertaining to a eukaryotic cell, preferably the cell is a fungal, mammalian or plant cell. Suitable eukaryotic cells include, for example, without limitation, mammalian cells, yeast cells (e.g., *Saccharomyces, Candida, Kluyveromyces, Schizosaccharomyces, Yarrowia, Pichia* and *Aspergillus*), or insect cells (including Sf9), amphibian cells (including melanophore cells), or worm cells including cells of *Caenorhabditis* (including *Caenorhabditis elegans*). Suitable mammalian cells include, for example, without limitation, COS cells (including Cos-1 and Cos-7), CHO cells, HEK293 cells, HEK293T cells, or other transfectable eukaryotic cell lines.

In embodiments pertaining to prokaryotes, preferably the cell is *E. coli*, a *Bacillus* sp., or *Streptomyces* sp. Preferably the *E. coli* host cell is an *E. coli* host cell that is recognized by the industry and regulatory authorities as suitable for recombinant protein expression (including but not limited to an *E. coli* K12 host cell or *E. coli* BL21 host cell). In certain embodiments, the recombinant host cell of this invention is *E. coli*. There are libraries of mutants, plasmids, detailed computer models of metabolism and other information available for *E. coli*, allowing for rational design of various modules to enhance product yield. Accordingly, in certain embodiments, a recombinant *E. coli* expressing a nucleic acid molecule encoding a GmSHC or GmSHC derivative coding sequence is provided for converting homofarnesol to ambroxan.

Another preferred host cell to use with the present disclosure is *S. cerevisiae*, which is widely used in synthetic biology. Thus, the recombinant host cell may be *S. cerevisiae*. There are libraries of mutants, plasmids, detailed computer models of metabolism and other information available for *S. cerevisiae*, allowing for rational design of various modules to enhance product yield. In addition, methods are known for making recombinant *S. cerevisiae* microorganisms. Accordingly, in certain embodiments, a recombinant *S. cerevisiae* expressing a nucleic acid molecule encoding a GmSHC or GmSHC derivative coding sequence is provided for converting homofarnesol to ambroxan.

Culturing of cells is performed in a conventional manner. The culture medium contains a carbon source, at least one nitrogen source and inorganic salts, and vitamins are added to it. The constituents of this medium can be the ones which are conventionally used for culturing the species of host cell in question. Carbon sources of use in the methods described herein include any molecule that can be metabolized by the recombinant host cell to facilitate growth and/or production of ambroxan. Examples of suitable carbon sources include, but are not limited to, sucrose (e.g., as found in molasses), fructose, xylose, glycerol, glucose, cellulose, starch, cellobiose or other glucose containing polymer.

In embodiments employing *E. coli*, a defined minimal medium such as M9A may be used for cell cultivation. The components of M9A medium include: 14 g/L $KH_2PO_4$, 16 g/L $K_2HPO_4$, 1 g/L $Na_3Citrate.2H_2O$, 7.5 g/L $(NH_4)_2SO_4$, 0.25 g/L $MgSO_4.7H_2O$, 0.015 g/L $CaCl_2.2H_2O$, 5 g/L glucose and 1.25 g/L yeast extract. In another embodiment of this disclosure, a nutrient-rich medium such as LB is used. The components of LB medium include: 10 g/L tryptone, 5 g/L yeast extract, 5 g/L NaCl. Other examples of Mineral Medium and M9 Mineral Medium are disclosed, for example, in U.S. Pat. No. 6,524,831 and US 2003/0092143.

In embodiments employing yeast as a host, for example, carbon sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

The suitability of a recombinant host cell for use in the methods of the present disclosure may be determined by simple test procedures using well-known methods. For example, the host cell to be tested may be propagated in a rich medium (e.g., LB-medium, Bacto-tryptone yeast extract medium, nutrient medium and the like) at a pH, temperature and under aeration conditions commonly used for propagation of the microorganism. Once a recombinant host cell is identified as producing the desired products of bioconversion, the products are typically produced by a production host cell line on the large scale by suitable expression systems and fermentations, e.g., by microbial production in cell culture.

The recombinant host cell may be grown in a batch, fed batch or continuous process or combinations thereof. As used herein, the term "batch cultivation" is a cultivation method in which culture medium is neither added nor withdrawn during the cultivation. By comparison, the term "fed-batch" means a cultivation method in which culture medium is added during the cultivation but no culture medium is withdrawn. Typically, the recombinant host cell is grown in a culture system, wherein the recombinant host cells are grown in fermentor at a defined temperature(s) in the presence of a suitable nutrient source, e.g., a carbon source, for a desired period of time to produce sufficient enzyme to bioconvert homofarnesol to ambroxan and to produce a desired amount of ambroxan including (–)-ambroxan. The recombinant host cells may be cultivated in any suitable manner, for example by batch cultivation or fed-batch cultivation. Often, however, higher cumulative production titers can be achieved by implementing a continuous process, such as product removal, substrate feed, and biomass addition or (partial) replacement.

One embodiment of the present disclosure provides a method of producing ambroxan in recombinant host cells by providing recombinant host cells expressing wild-type GmSHC or a GmSHC derivative in a culture system, providing homofarnesol to the culture system (e.g., by feeding), converting homofarnesol to ambroxan using the GmSHC or GmSHC derivative produced by the recombinant host cells, collecting ambroxan and optionally isolating the ambroxan (in particular, (–)-ambroxan). In some embodiments, the recombinant host cell also expresses other nucleic acid molecules that serve to enhance the expression of GmSHC or bioconversion pathway for making ambroxan.

Another embodiment of the present disclosure provides a method of producing ambroxan in recombinant host cells by providing recombinant host cells expressing wild-type GmSHC or a GmSHC derivative in a culture system, providing homofarnesol to the culture system, feeding homofarnesol (e.g., EEH) to the culture system in the presence of a solubilizing agent suitable to promote the conversion of homofarnesol to ambroxan, collecting ambroxan and optionally isolating the ambroxan (in particular, (–)-ambroxan). In some embodiments, conversion is enhanced by the adding a solubilizing agent, in particular a non-ionic surfactant or detergent such as polysorbate 80 sold under the tradename TWEEN® 80, t-octylphenoxypolyethoxyethanol sold under the tradename TRITON® X-100 and the like, to the reaction mixture.

The recombinant host cells may be cultured in a number of ways in order to provide cells in suitable amounts expressing the wild-type GmSHC or GmSHC derivative for the subsequent bioconversion step. Since the host cells applicable for the bioconversion step vary broadly (e.g., fungal, bacterial, insect, mammalian and plant cells), culturing conditions are, of course, adjusted to the specific requirements of each species and these conditions are well-known and documented. Any of the art known methods for growing recombinant host cells may be used to produce the cells used in the subsequent bioconversion step of the present disclosure. Typically the cells are grown to a particular density (measurable as optical density (OD)) to produce a sufficient biomass for the bioconversion reaction.

The cultivation conditions chosen can influence the amount of cells obtained (the biomass) as well as how the biomass becomes a biocatalyst (i.e., a cell or cell fraction containing a wild-type GmSHC or GmSHC derivative). In some embodiments, the biocatalyst is a recombinant whole cell that expresses wild-type GmSHC or GmSHC derivative. In other embodiments, the biocatalyst is a recombinant whole cell suspension or immobilized cell that expresses wild-type GmSHC or GmSHC derivative. In other embodiments, the biocatalyst is a membrane fraction or a liquid fraction prepared from the recombinant host cell that expresses a wild-type GmSHC or GmSHC derivative. The recombinant whole cell producing a wild-type GmSHC or GmSHC derivative include whole cells collected from the fermentor (for the bioconversion reaction) or the cells in the fermentor (which are then used in a one-pot reaction). The recombinant whole cell producing a wild-type GmSHC or GmSHC derivative can include intact recombinant whole cell and/or cell debris. Either way, the wild-type GmSHC or GmSHC derivative is associated with a membrane (such as a cell membrane) in some way in order to receive and/or interact with a substrate (e.g., homofarnesol), which membrane (such as a cell membrane) can be part of or include a whole cell (e.g., a recombinant whole cell). The wild-type GmSHC or GmSHC derivative may also be in an immobilized form (e.g., associated with an enzyme carrier) which allows the wild-type GmSHC or GmSHC derivative to interact with a substrate (e.g., homofarnesol). The wild-type GmSHC or GmSHC derivative may also be used in a soluble form.

In one embodiment, the biocatalyst is produced in sufficient amounts (to create a sufficient biomass), harvested and washed (and optionally stored (e.g., frozen or lyophilized)) before the bioconversion step. In a further embodiment, the cells are produced in sufficient amounts (to create a sufficient biocatalyst) and the reaction conditions are then adjusted without the need to harvest and wash the biocatalyst for the bioconversion reaction. This one step (or "one pot") method is advantageous as it simplifies the process while reducing costs. The culture medium used to grow the cells is also suitable for use in the bioconversion reaction provided that the reaction conditions are adjusted to facilitate the bioconversion reaction.

The optimum pH for growing the cells is in the range of 6.0-7.0. The optimum pH for the bioconversion reaction may be dependent on the SHC enzyme used in the bioconversion reaction, e.g., wild-type GmSHC or GmSHC derivative. The pH is regulated using techniques which are well-known to the skilled person.

While the terms "mixture" or "reaction mixture" may be used interchangeably with the term "medium" in the present disclosure (especially as it relates to a "one pot" reaction), it should be noted that growing the cells to create a sufficient biomass requires a cell culture/fermentation medium but a medium is not required for the bioconversion step as a reaction buffer will suffice at a suitable pH.

The bioconversion methods of the present disclosure are carried out under conditions of time, temperature, pH and solubilizing agent to provide for conversion of the homofarnesol feedstock to ambroxan. The pH of the reaction mixture may be in the range of 4 to 8, preferably, 5 to 6.5, more preferably 4.8 to 6.0 for the GmSHC derivative enzymes and in the range of from about pH 5.0 to about pH 7.0 for the wild-type GmSHC enzyme and can be maintained by the addition of buffers to the reaction mixture. The buffer used may be a citrate, phosphate, TRIS (tris(hydroxymethyl)aminomethane), or MES (2-(N-morpholino) ethanesulfonic acid) buffer. In certain embodiments, the buffer is Tris-Cl buffer. The preferred temperature is between from about 15° C. and about 45° C., preferably about 20° C. and about 40° C. The temperature can be kept constant or can be altered during the bioconversion process.

The use of a solubilizing agent, e.g., a surfactant, detergent, solubility enhancer, water miscible organic solvent and the like, has been shown to improve in the bioconversion reaction. As used herein, the term "surfactant" means a component that lowers the surface tension (or interfacial tension) between two liquids or between a liquid and a solid. Surfactants may act as detergents, wetting agents, emulsifiers, foaming agents, and dispersants. In certain embodiments, the surfactant is a nonionic surfactant, anionic surfactant, cationic surfactant or amphoteric or zwitterionic surfactant. Examples of nonionic surfactants include, but are not limited to, t-octylphenoxypolyethoxyethanol sold under the tradename TRITON® X-100 (4-(1,1,3,3-Tetramethylbutyl)phenyl-polyethylene glycol, Polyethylene glycol tert-octylphenyl ether), polysorbate 80 sold under the tradename TWEEN® 80, and polysorbate 20 sold under the tradename TWEEN® 20. Exemplary anionic surfactants include, but are not limited to, taurodeoxycholate, sodium taurodeoxycholate, sodium dodecyl sulfate (SDS), and sodium lauryl sulfate (SLS). As the results presented herein demonstrate, t-octylphenoxypolyethoxyethanol sold under the tradename TRITON® X-100 is a particularly useful solubilizing agent. Accordingly, t-octylphenoxypolyethoxyethanol sold under the tradename TRITON® X-100 and other surfactants such as SDS and polysorbate 20 sold under the tradename TWEEN® 20 can be used to increase the velocity and yield for the homofarnesol to ambroxan bioconversion reaction. The solubilizing agent can be included at a concentration range of about 0.005% to 0.48% in the reaction, or more preferably about 0.05 to 5% in the reaction mixture.

According to the methods of this invention, ambroxan is produced using a biocatalyst to which the homofarnesol substrate is added. It is possible to add the substrate by feeding using known means (e.g., peristaltic pump, infusion syringe and the like). Homofarnesol is an oil soluble compound and is provided in an oil format. Given that the biocatalyst (microbial cells such as intact recombinant whole cell and/or cell debris and/or immobilized enzyme) is present in an aqueous phase, the bioconversion reaction may be regarded as a three phase system (including an aqueous phase, a solid phase and an oil phase) when homofarnesol is added to the bioconversion reaction mixture. This may also be the case even when solubilizing agent is present.

While some embodiments include the use of whole intact cells or cell extracts, other embodiments include the use of free, optionally purified or partially purified GmSHC enzyme or immobilized GmSHC enzyme for bioconversion of homofarnesol to ambroxan. In this respect, when a soluble wild-type GmSHC or a GmSHC derivative is used as a biocatalyst, this is considered a two phase system.

The number of homofarnesol isomers present may influence the speed of the reaction. It has been demonstrated that a SHC derivative enzyme is capable of bioconverting E,E-homofarnesol to (–)-ambroxan from a complex mixture of homofarnesol isomers (e.g., EE:EZ:ZE:ZZ) (see WO 2016/170099). However, a lower conversion rate is typically observed using the complex mixture of homofarnesol isomers, which is consistent with the view that homofarnesol isomers other than EEH may compete with EEH for access to the SHC derivative enzyme and thus may act as competitive inhibitors for the conversion of EEH to (–)-ambroxan and/or also act as alternative substrates. Accordingly, the present method is preferably carried out in the presence of a homofarnesol substrate composed of a stereoisomeric mixture of 2-4 isomers, preferably two isomers. In some embodiments, only two isomers of homofarnesol are added to the reaction mixture. In certain embodiments, the homofarnesol substrate is composed of an EE:EZ stereoisomeric mixture. In other embodiments, stereoisomerically pure E,E-homofarnesol is added to the reaction mixture.

The ambroxan produced by the method of this invention may be collected, e.g., steam extraction/distillation or organic solvent extraction using a non-water miscible solvent (to separate the reaction products and unreacted substrate from the biocatalyst which stays in the aqueous phase) followed by subsequent evaporation of the solvent to obtain a crude reaction product as determined by gas chromatographic (GC) analysis. Steam extraction/distillation and organic solvent extraction methods are known to those skilled in the art. By way of illustration, the resulting ambroxan may be extracted from the whole reaction mixture using an organic solvent such as a non-water miscible solvent (e.g., toluene). Alternatively, the resulting ambroxan may be extracted from the solid phase of the reaction mixture (obtained by, e.g., centrifugation or filtration) using a water miscible solvent (e.g., ethanol) or a non-water miscible solvent (e.g., toluene). By way of further example, ambroxan is present in the solid phase as crystals or in amorphous form and can be separated from the remaining solid phase (cell material or debris thereof) and the liquid phase also by means of filtration. By way of further example, at a temperature above the melting point of ambroxan (approximately 75° C.), the ambroxan may form an oil layer on top of aqueous phase, wherein the oil layer can be removed and collected. In order to ensure a complete recovery of ambroxan after the oil layer is removed, an organic solvent may be added to the aqueous phase containing the biomass in order to extract any residual ambroxan contained in, or on or about the biomass. The organic layer can be combined with the oil layer, before the whole is further processed to isolate and purify ambroxan. The ambroxan may be further selectively crystallized to remove by-products (i.e., isomers other than (–)-ambroxan) and any unreacted homofarnesol substrate from the final product. The term "selective crystallization" refers to a process step whereby (–)-ambroxan is caused to crystallize from a solvent while the remaining isomers remain dissolved in the crystallizing solvent. In some embodiments, the isolated crystalline material contains only (–)-ambroxan product. In other embodiments, the isolated crystalline material contains the other isomers, wherein said isomers are present only in olfactory acceptable amounts.

Examples of suitable water miscible and non-water miscible organic solvents suitable for use in the extraction and/or selective crystallization of (–)-ambroxan include, but are not limited to, aliphatic hydrocarbons, preferably those having 5 to 8 carbon atoms, such as pentane, cyclopentane, hexane, cyclohexane, heptane, octane or cyclooctane; halogenated aliphatic hydrocarbons, preferably those having one or two carbon atoms, such as dichloromethane, chloroform, carbon tetrachloride, dichloroethane or tetrachloroethane; aromatic hydrocarbons, such as benzene, toluene, the xylenes, chlorobenzene or dichlorobenzene; aliphatic acyclic and cyclic ethers or alcohols, preferably those having 4 to 8 carbon atoms, such as ethanol, isopropanol, diethyl ether, methyl Cert-butyl ether, ethyl Cert-butyl ether, dipropyl ether, diisopropyl ether, dibutyl ether, tetrahydrofuran; or esters such as ethyl acetate or n-butyl acetate or ketones such as methyl isobutyl ketone or dioxane or mixtures of these. The solvents that are especially preferably used are the above-mentioned heptane, methyl Cert-butyl ether (also known as MTBE, tertiary butyl methyl ether and iBME), diisopropyl ether, tetrahydrofuran, ethyl acetate and/or mixtures thereof. Preferably, a water miscible solvent such as ethanol is used for the extraction of (−)-ambroxan from the solid phase of the reaction mixture. The use of ethanol is advantageous because it is easy to handle, it is nontoxic and it is environmentally friendly.

In certain embodiments, the final product is isolated (−)-ambroxan. The term "isolated" as used with reference to (−)-ambroxan, refers to a bioconversion product that has been separated or purified from components which accompany it. An entity that is produced in a cellular system different from the source from which it naturally originates is "isolated" because it will necessarily be free of components which naturally accompany it. The degree of isolation or purity can be measured by any appropriate method, e.g., gas chromatography (GC), HPLC or NMR analysis. In some embodiments, the end product ((−)-ambroxan) is isolated and purified to homogeneity, e.g., at least 80%, 81%, 82%, 83%, 84%, 85%, 86%, 87%, 88%, 89%, or 89.5% pure or 90%, 91%, 92%, 93%, 94%, 95%, 96%, 97%, 98%, 99%, or 99.5% pure.

The olfactive purity of the final (−)-ambroxan product may be determined using a 10% ethanol extract in water or by testing the crystalline material. The final (−)-ambroxan product may be tested against a commercially available reference of (−)-ambroxan product for its olfactive purity, quality and its sensory profile. The (−)-ambroxan material can also be tested in application studies by experts in order to determine if the material meets the specifications with respect to its organoleptic profile.

The activity of the GmSHC enzyme is defined via the reaction rate (amount of product/(amount of product+amount of remaining starting material))×100) in mol percent. Preferably, the bioconversion of EEH into (−)-ambroxan in the presence of wild-type GmSHC or a GmSHC derivative enzyme, or in the presence of a recombinant host cell that expresses a wild-type GmSHC or a GmSHC derivative, provides an (−)-ambroxan yield of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, given in mol percent and based on the mols of EEH employed; especially preferably, the yield is between 5 and 100, 10 and 100, 20 and 100, 25 and 100, 30 and 100, 35 and 100, in particular between 40 and 100, 45 and 100, 50 and 100, 60 and 100, 70 and 100.

In a preferred embodiment of the invention, the yield and/or the reaction rate are determined over a defined time period of, for example, 4, 6, 8, 10, 12, 16, 20, 24, 36 or 48 hours, during which EEH is converted into (−)-ambroxan by a recombinant host cell harboring a nucleic acid molecule encoding a wild-type GmSHC or a GmSHC derivative enzyme according to the present disclosure. In a further embodiment, the reaction is carried out under defined conditions of, for example, 25° C., 30° C., 40° C., 50° C. or 60° C.

The bioconversion process for making (−)-ambroxan from homofarnesol in a recombinant strain of *E. coli* harboring a nucleic acid molecule encoding a wild-type GmSHC or a GmSHC derivative enzyme can offer a low cost and industrially economical process for (−)-ambroxan production.

Desirably, the amount of (−)-ambroxan produced is in the range of about 1 mg/L to about 20,000 mg/L (20 g/L) or higher such as from about 20 g/L to about 200 g/L or from 100 to 200 g/L, preferably about 125 g/L or 150 g/L.

Various applications for (−)-ambroxan include, but are not limited to, a fine fragrance or a consumer product such as fabric care, toiletries, beauty care and cleaning products including essentially all products where the currently available ambroxan ingredients are used commercially, including but not limited to, AMBROX (Firmenich), Ambroxan (Henkel) AMBROFIX (Givaudan), AMBERLYN (Quest), CETALOX Laevo (Firmenich), AMBERMOR (Aromor) and/or Norambrenolide Ether (Pacific) products. The selective crystallization of (−)-ambroxan may be influenced by the presence of unreacted homofarnesol substrate and also the ratio of (−)-ambroxan to the other detectable isomers. Even if only 10% conversion of the homofarnesol substrate to (−)-ambroxan is obtained, the selective crystallization of (−)-ambroxan is still possible.

The following non-limiting examples are provided to further illustrate the present invention.

Example 1: Insertion of a PelB Leader Sequence

As one approach to increasing the enzyme activity of GmSHC, a pelB leader sequence was inserted into the pET28b(+) vector containing nucleic acids encoding GmSHC. An oligonucleotide encoding the pelB leader sequence was prepared with NcoI and NdeI compatible ends for insertion into the pET28b(+) vector. The pET28b(+) vector was digested with NcoI and NdeI and used in an overnight ligation reaction with the pelB leader sequence oligonucleotide. The ligation reaction was purified and used in the transformation of electrocompetent *E. coli*. A random sample of the resulting transformant *E. coli* was assessed by colony PCR with complimentary oligonucleotide primers 'pelB-SHC-Fw' and 'pET-XhoI-Rev' to determine whether the ligation reactions were successful. A clone was identified as containing an insert of the correct size. Subsequent DNA sequence analysis confirmed the insertion of a pelB leader sequence into the pET28b(+) vector.

Example 2: Expression Analysis of the PelB-GmSHC Fusion Protein

The plasmid containing the pelB-GmSHC clone was used to transform *E. coli* BL21(DE3) for expression of the fusion protein. Following transformation, a single colony clone was isolated and used to inoculate 10 mL of LB medium+kanamycin. The 10 mL culture was incubated at 37° C., with shaking at 200 rpm overnight. The overnight culture was used to inoculate a flask containing 1 L of LB medium+kanamycin, which was incubated at 37° C., with shaking at 200 rpm for 6 hours prior to induction. Induction of protein expression was initiated by the addition of 1 mL of 1 M IPTG. Following induction, the incubator temperature was dropped to 25° C. and the culture was left overnight with shaking at 200 rpm. An aliquot (1.5 mL) of the 25° C.

overnight culture was removed for expression analysis by SDS-PAGE, the remaining culture was harvested by centrifugation for further work. From SDS-PAGE analysis, it was observed that a pelB-GmSHC fusion protein of the correct size was expressed.

Example 3: Whole Cell Screening Assays

The pelB leader sequence was included to facilitate the transport of the GmSHC enzyme into the E. coli periplasmic space thereby making the GmSHC enzyme more available to substrates in the environment surrounding the cells. Accordingly, screening assays were carried to analyze the conversion of homofarnesol to ambroxan by whole cell suspensions containing pelB-GmSHC as compared to GmSHC. Reactions included whole cells, 100 µl of 1 M Sodium Citrate, pH 4.9, 100 µl of 100 mM homofarnesol in Solubilization Buffer (0.05 M Tris-Cl, pH 8.0, 0.01 M $MgCl_2$, 1% v/v t-octylphenoxypolyethoxyethanol sold under the tradename TRITON® X-100) and 800 µl of Solubilization Buffer. The reactions were incubated at 37° C., 200 rpm and samples were removed after 16 and 80 hours. The samples were extracted with 2 volumes of n-heptane prior to GC analysis. The average % area conversion per mg of whole cell was calculated. The results indicated that whereas the wild-type GmSHC cell suspensions provided an average 0.033% area per mg whole cell per hour, pelB-GmSHC cell suspensions did not result in any conversion of homofarnesol to ambroxan. Accordingly, the pelB leader sequence appeared to adversely affect the activity of GmSHC.

As SHC enzymes are co-factor independent, it was posited that GmSHC may retain activity post-reaction. To determine whether any activity was retained, cells from the 16-hour time point described above were removed and resuspended in 0.5 mL of fresh reaction mixture. These '$2^{nd}$ pass' reactions were then incubated at 37° C., 200 rpm for approximately 64 hours. After 64 hours, the reactions were extracted with 2 volumes of n-heptane for GC analysis. The comparison of the '$1^{st}$ pass' and '$2^{nd}$ pass' indicated minimal degradation of activity following repeat exposure to fresh reaction mixture (0.033% at $1^{st}$ pass versus 0.037% at $2^{nd}$ pass). Accordingly, these data indicate that the whole cells can be reused/recycled to perform repeat conversions, which may prove advantageous to minimizing the overall cost of the process.

Example 4: Conversion of Homofarnesol to Ambroxan in the Fermentation

As demonstrated above, whole cells expressing GmSHC bioconverted homofarnesol to ambroxan. Accordingly, it was determined whether conversion in the fermentation could be achieved. Cells expressing wild-type GmSHC or R. palustris SHC (RpSHC; WO 2010/139719) were grown and expressed in the following manner. Overnight 10 mL (LB medium+kanamycin, 37° C., 200 RPM) starter cultures of the cells harboring nucleic acids encoding GmSHC and RpSHC were used to inoculate 1 L of LB medium+kanamycin. The 1 L cultures were incubated at 37° C., 200 rpm for approximately 4 hours. Subsequently, 1 mL of 1M IPTG was added to the cultures to induced SHC protein expression and the incubation temperature of the culture was reduced to 25° C. for the overnight incubation.

To confirm expression of GmSHC and RpSHC, analysis by SDS-PAGE was performed on the cell culture. Aliquots (1.5 mL) of the overnight culture were removed and centrifuged at 14,500 rpm for 2 minutes. The supernatant was discarded and the cell pellets were resuspended in 200 µL of SDS loading buffer. The resuspended cells were then heated to 95° C. for 5 minutes. Following a brief centrifugation, 14,500 rpm for 10 seconds, samples of the SHCs in loading buffer were placed into the wells of a pre-cast 4-20% SDS-PAGE gel. The results of this analysis indicated that both GmSHC and RpSHC were expressed.

Following confirmation of expression of GmSHC and RpSHC, duplicate reactions were prepared as provided in Table 3.

TABLE 3

| Reaction Contents | Set A | Set B |
|---|---|---|
| Cell Culture* | 850 µL | 850 µL |
| 1M Na Citrate, pH 4.9 | 100 µL | 100 µL |
| 100 mM Homofarnesol in 0.05M Tris-Cl, pH 8.0, 0.01M $MgCl_2$, 1% v/v t-octylphenoxypolyethoxyethanol sold under the tradename TRITON® X-100 | 50 µL | — |
| *100 mM Homofarnesol in 0.1M Na Citrate, pH 6.5, 2% Taurodeoxycholate | — | 50 µL |

*Emulsion described in WO 2010/139719.

The reactions were prepared and incubated at 37° C., 200 rpm. Samples were removed after 16 hours incubation and extracted with 2 volumes of n-heptane for GC analysis. After 40 hours, the remaining reaction mixture was centrifuged to pellet the cells and the supernatant was extracted with 2 volumes of n-heptane for GC analysis. The averages of the % area conversion per hour are presented in Table 4.

TABLE 4

| SHC Culture | Set A | Set B |
|---|---|---|
| GmSHC | 0.46 | 0.00 |
| RpSHC | 0.10 | 0.00 |

The results presented in Table 4 demonstrate conversion of homofarnesol to ambroxan by the SHCs in cell culture medium. The results also demonstrate that homofarnesol in t-octylphenoxypolyethoxyethanol sold under the tradename TRITON® X-100 was more readily converted to ambroxan than as an emulsion in taurodeoxycholate.

Example 5: Rational Design of GmSHC Derivatives

Homology Modeling.

The three dimensional structure of GmSHC was build using homology modeling. The templates used were the crystals 1GSZ (Lenhart, et al. (2002) Chem. Biol. 9:639-45) and 3SQC (Wendt, et al. (1999) J. Mol. Biol. 286:175-87), which share 44% and 43% of sequence identity with 95% of GmSHC sequence.

Molecular Docking.

The ground state representations of homofarnesol was then docked to the active center of the GmSHC structure. This was achieved by defining a 3D grid box centered in the protonated oxygen atom of the first proton donor. This grid box identifies the active center pocket area where the substrates conformations will be sampled during the molecular docking run. Then molecular docking was performed using the Lamarckian genetic algorithm (LGA; Morris, et al. (1998) J. Comput. Chem. 19:1639-62; Morris, et al. (2009) J. Comput. Chem. 30:2785-91). A total of 1000

LGA runs were carried out per system. The population was 300, the GA elitism=1, the maximum number of generations was 27000 and the maximum number of energy evaluations was 2500000. Accordingly, for each LGA run the first generation started with a population of 300 random substrates conformations. The best substrate conformation in the current population automatically survives into the next generation (GA elitism=1). As such, the next generation population starts with the fittest substrate conformation from the previous generation plus another 299 conformations. The LGA run stops when the number of maximum generations or energy evaluations are reached. For each LGA run, one substrate conformation was obtained. Substrate conformations were then sorted according to energy and root mean square deviation. The top ranked structure corresponded to the lowest binding energy structure of the most populated cluster with the lowest mean binding energy.

SHC Structural Analysis and Catalytic Mechanism.

SHCs are integral monotopic membrane proteins which adopt a dimeric 3D arrangement. Each monomer is characterized by eight QW motifs (Sato, et al. (1998) Biosci. Biotechnol. Biochem. 62:407-11) that tightly connect numerous α-helices building up two highly stable α/α-barrels domains (Wendt, et al. (1999) J. Mol. Biol. 286:175-87). The active center cavity is buried within the two α/α-barrels domains and its access is possible through an inner hydrophobic channel. For AaSHC, the channel and the active center cavity are separated by a narrow constriction constituted by residues F166, V174, F434, and C435, which is responsible for substrate recognition (Lenhart, et al. (2002) Chem. Biol. 9:639-45). For GmSHC, those residues correspond to F176, M184, F457 and C458. Unless indicated otherwise, the position of the amino acid residues provided with respect to GmSHC are with reference to SEQ ID NO:2. At the top of the activity center cavity, the residues that constitute the conserved DXDD motif (Wendt, et al. (1999) J. Mol. Biol. 286:175-87) are observed. One of those residues is D396, the first proton donor, which initiates the cyclization by donating a proton to the double bond 2 and 3 (Scheme 2). In GmSHC, the oxygen atom of D396 is 4.6Å from the carbon 3 of the double bond 2,3.

SCHEME 2

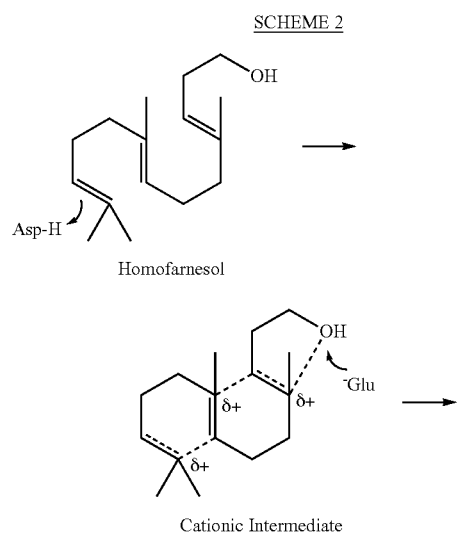

Homofarnesol

Cationic Intermediate

-continued

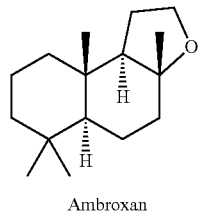

Ambroxan

The DXDD motif is followed by tryptophan and phenylalanine residues that are responsible for stabilizing the cationic intermediates by strong cation-n interactions (Dougherty (1996) Science 271:163-168). On the bottom of the cavity is a Glutamate residue, the last proton acceptor, which may receive a proton from the hydroxyl group and lead to the closing of the third ring and formation of the product, Ambrox. Structural analysis of GmSHC indicates that this enzyme possesses two possible last proton acceptors. However, according to the docking results, E386 of GmSHC is the most likely the last proton acceptor. The distance between the homofarnesol hydroxyl oxygen and E386 is just 3.5Å. Clearly this disposition of the last proton acceptor plays an important role in the catalytic efficacy of this enzyme.

Using the molecular model, GmSHC residues that establish the cation-pi interactions responsible for the stabilization of the cationic intermediate and the other main catalytic residues were determined. Notably, the important catalytic residues are conserved with other SHC enzymes. The main differences include: a) the GmSHC active center is residue 45; b) GmSHC residue 184, together with residues 176, 457 and 458, is responsible for the narrow constriction between the hydrophobic channel and the active center cavity, which is associated with substrate selectivity; and c) the pattern of QW motifs is somewhat different.

Structural Hotspots.

Based on the molecular modeling and molecular docking results, the following structural hotspots were identified: residues V45, E46, Q54, F176, M184, F457, C458, W179, I278, Q279, T326, F385, E386, D397, F443, F460, F624, F654 and L656.

Specificity Determining Positions and Conserved Residues.

The specificity determining positions indicate which residues coordinately evolved within a subgroup of proteins of a family that shares a given catalytic specificity. Thus, it allows following the evolutionary process associated with acquiring a diversity of biological functions within the same family of proteins. Specificity determining positions were calculated from a multiple sequence alignment containing 1000 homologous sequences using the algorithms of Xdet. The specificity determining positions of GmSHC are: Y113, V138, R141, F171, E225, E226, D227, Q324, G381, I455, H474, L476, S559, A568, L656 and E679.

Evolution of GmSHC.

To improve the catalytic conversion of homofarnesol to ambrox, GmSHC was modified to (1) improve the Michaelis-Menten complex; (2) introduce mutations that can increase the cation-n stabilization of the carbocation intermediate, based on the structural and coevolution hotspots; (3) open the catalytic cavity by mutating the residues that are only essential for the catalysis of the 5-ring native substrate, squalene; (4) mutate the residues that assist the last proton acceptor in order to facilitate product formation; (5) alter the active center; (6) mutate residues responsible for the narrow constriction between the hydrophobic channel and the active center cavity; (7) and increase the QW motifs.

GmSHC variants designed to improve the Michaelis-Menten complex and increase the cation-π stabilization of the carbocation intermediate were tested in silico using molecular docking. The results of this analysis are presented in Table 5.

TABLE 5

| SHC mutant | Calculated Affinity (Kcal/mol) | Comments |
|---|---|---|
| WT | −6.01 | — |
| I278F | −6.30 | Substrate is closer to the first proton donor. |
| V45I | −6.05 | Similar to WT. |
| V45F | −6.38 | Substrate is closer to the first proton donor. |
| L656W | −6.14 | Substrate is closer to the first proton donor; Different last proton acceptor. |
| L656F | −6.22 | Substrate is closer to the first proton donor; Different last proton acceptor. |
| W179A | −6.45 | Substrate is closer to the first proton donor; Different last proton acceptor. |
| I278A | −6.26 | Substrate is closer to the first proton donor. |
| F654Y |  | Designed to increase cation-π interactions. Substrate pose similar to WT. |
| I278N | −6.43 | Substrate is closer to the first proton donor; Same last proton acceptor but the substrate hydroxyl also interacts with I278N. |
| T326N | −6.15 | Substrate is closer to the first proton donor; Same last proton acceptor but now T326N improves polarity surrounding the last proton acceptor. |
| L656E | −6.06 | Substrate is closer to the first proton donor; L656E last proton acceptor. |
| G623A | −6.41 | Substrate is closer to the first proton donor and to the last proton acceptor. |
| F460A | −6.13 | Opens the lower part of the active center cavity. The substrate pose is similar to WT. |
| F443Y | −5.94 | Designed to increase cation-π interactions. |
| E386H | −6.11 | Different last proton acceptor. |

Additional mutations addressing each of the modifications indicated above are listed Table 6.

TABLE 6

| Functional Change | GmSHC Mutation |
|---|---|
| (1) improve the Michaelis-Menten complex | V45I |
|  | V45L |
|  | V45Q |
|  | V45A |
|  | E46Q |
|  | E46A |
|  | E46H |
|  | Q54E |
|  | Q54H |
|  | G623A |
|  | G623V |
|  | F385Y |
|  | E386D |

TABLE 6-continued

| Functional Change | GmSHC Mutation |
|---|---|
|  | E386Q |
|  | E386H |
|  | E386N |
|  | F443I |
|  | F443L |
|  | F443A |
|  | F443V |
|  | F443H |
|  | F443Y |
|  | F624W |
|  | F624A |
|  | F624Y |
|  | L656F |
|  | L656Y |
|  | L656I |
|  | L656W |
|  | L656E |
|  | L656N |
|  | V45Q + L656E |
|  | V45L + T326S |
|  | T326D + E386T |
|  | F385Y + F654Y |
| (2) introduce mutations that can increase the cation-π stabilization of the carbocation intermediate, based on the structural and coevolution hotspots | F654W |
|  | F654A |
|  | F654L |
|  | F654Y |
| (1) improve the Michaelis-Menten complex; and | W179A |
|  | W179V |
| (2) introduce mutations that can increase the cation-π stabilization of the carbocation intermediate, based on the structural and coevolution hotspots |  |
| (1) improve the Michaelis-Menten complex; and (4) mutate the residues that assist the last proton acceptor in order to facilitate product formation | T326E |
|  | T326D |
|  | T326S |
|  | T326N |
|  | T326C |
|  | T326N + I278N |
| (2) introduce mutations that can increase the cation-π stabilization of the carbocation intermediate, based on the structural and coevolution hotspots; (3) open the catalytic cavity by mutating the residues that are only essential for the catalysis of the 5-ring native substrate, squalene; and (4) mutate the residues that assist the last proton acceptor in order to facilitate product formation | I278A |
|  | I278V |
|  | I278F |
|  | I278Y |
|  | I278N |
| (5) alter the active center | Q178H |
|  | Q178E |
|  | Q178D |
|  | D397C |
|  | D397C + D394V + V471C |
| (6) mutate residues responsible for the narrow constriction between the hydrophobic channel and the active center cavity | M184L |
|  | M184V |
|  | M184I |
|  | M184C |
|  | M184A |
| (7) and increase the QW motifs | R194Q |
|  | M305W |
|  | S321W |
|  | S321F |
|  | P412Q |
|  | M345W |
| Other | W87L |
|  | W87V* |
|  | L335F |
|  | F460A |
|  | F460H |
|  | F460L |
|  | Y658F |
|  | W556A |
|  | W556V* |
|  | Q279V + Q54V |
|  | D397C + D394V |
|  | F385H + E386A |

TABLE 6-continued

| Functional Change | GmSHC Mutation |
|---|---|
| | F385E + E386A |
| | F385Y + F654Y + F443Y |

*From the literature.

SHC Mutant Enzyme Expression.

Wild-type and the GmSHC mutants of Table 6 were individually cloned into pET28a(+). These DNA constructs were transformed into BL21(DE3) *E. coli* and plated onto agar plates containing Kanamycin. These were incubated overnight at 37° C. A single bacterial colony was picked and used to inoculate 500 µL LB+Kanamycin in a 96-well plate. This plate was incubated overnight at 37° C. with agitation. These primary cultures (10 µL) were used to inoculate 10 mL LB+Kanamycin in a 50 mL falcon tube, which was subsequently incubated at 37° C. at 180 rpm for about 7 hours. Protein expression was then induced with the addition of 1 mM IPTG. The incubator temperature was lowered to 25° C. and the cultures further incubated at 180 rpm overnight. The next day, the cultures were centrifuged at 4000 rpm for 10 minutes and the supernatant discarded. Cell pellets were exposed to 2 rounds of freeze/thawing before use in the reaction assay.

Cell pellet (1 µL) was spotted onto a nitrocellulose membrane and allowed to air dry for 30 minutes. The membrane was placed into 5% milk powder for 1 hour at room temperature with gentle agitation. The membrane was then rinsed with phosphate-buffered saline (PBS), 3×5 minutes. Anti-histidine antibody solution (1 in 10,000 dilution) was added and incubated at room temperature for 1 hour with shaking. The blot was subsequently washed in PBS, 3×5 minutes. Developing solution (6 mg diaminobenzidine (DAB) and 5 µL 30% $H_2O_2$ in 10 mL PBS) was added to the blot. Once developed, the developing solution was immediately removed and the blot rinsed with water.

The results of this analysis indicated that all constructs were expressed in BL21 (DE3) *E. coli* at 25° C. following the addition of 1 mM IPTG. Following expression and processing of the enzymes, a dot blot was performed to assess if the introduction of specific mutations had altered the protein expression. Notably, the majority of the GmSHC mutants showed similar levels of expression to the wild-type GmSHC construct.

SHC Mutant Screening Reactions.

Sodium citrate buffer pH 5.3 (equal volumes of 1 M sodium citrate, pH 4.9 and 0.1 M sodium citrate, pH 6.5) was prepared. Taurodeoxycholate (2% w/w with respect to homofarnesol substrate) was then added to the sodium citrate buffer. Subsequently, homofarnesol (3, 10 or 15 mg/mL) was added to the buffer. The resulting emulsion was transferred into two 96-well plates and incubated at 37° C. with agitation for various time periods depending on the homofarnesol concentration added, i.e., 3 mg/mL homofarnesol, 16-hour incubation; 10 mg/mL homofarnesol, 6- and 24-hour incubations; 15 mg/mL homofarnesol, 4- and 20-hour incubations. The Homofarnesol concentration was increased and the incubation period decreased as the study progressed allowing for more apparent differences in SHC activity between the mutants investigated. To stop the reaction and extract the products, a 2× volume of heptane was added to each well. The plate was then incubated at 37° C. for 30 minutes with agitation to mix thoroughly. The plate was centrifuged for 10 minutes at 4000 rpm to pellet any cellular material. The upper organic layer was then removed and placed in a clean gas chromatography (GC) vial.

GC Analysis Method.

A GC analytical method was used to detect each of the starting materials and products used in the screening reactions. Due to the volume of samples generated, a fast method was developed with a run time of only 4.5 minutes. The GC analysis conditions are presented in Table 7.

TABLE 7

| Component | Condition | | |
|---|---|---|---|
| GC system | Perkin Elmer Autosystem XL | | |
| Column | Agilent HP-5 (30 m, 0.25 mm × 0.25 µm) | | |
| Carrier gas | Helium | | |
| Carrier pressure | 30 psi | | |
| Oven program | Rate/° C. min$^{-1}$ | Temperature/° C. | Hold/min |
| | 0 | 200 | 1.5 |
| | 45 | 225 | 0.5 |
| Injection temperature | 270° C. | | |
| Detector | FID | | |
| Detector temperature | 270° C. | | |
| Injection volume | 1 µL | | |
| Syringe volume | 10 µL | | |
| Data acquisition time | 4.5 minutes | | |

Analysis of the SHC mutant reaction samples following the addition of both 3 and 10 mg/mL homofarnesol indicated that a number of SHC mutants/derivatives exhibited improved activity compared to the wild-type enzyme. Mutants of particular interest are listed in Table 8.

TABLE 8

| Mutation | Average increase in ambroxan production vs SHC WT (% peak area) |
|---|---|
| M184A | +21 |
| F624Y | +21 |
| V45L + T326S | +18.5 |
| M184L | +18.5 |
| E46H | +18 |
| Q54E | +18 |
| R194Q | +14.5 |
| F624A | +14 |
| Y658F | +14 |
| G623A | +14 |
| M184I | +13 |
| Q178E | +12.5 |
| E46Q | +12.5 |
| M184V | +11 |
| F460A | +6 |

The results demonstrated that many of the enzymes reached full consumption of the homofarnesol isomer used to generate the ambroxan. Accordingly, further analysis was conducted to identify one or more optimal SHC enzymes. In particular, substrate loading was increased to 15 mg/mL and incubation was allowed to progress for a limited period of time (i.e., 4 hours and 20 hours). As shown in Table 9, there were multiple mutant enzymes which displayed higher activity than the wild-type SHC enzyme. In particular, the F624Y SHC mutant showed the highest activity after 4 hours, whereas the E46Q SHC mutant showed the highest activity after 20 hours. Notably, each the enzymes with mutations at position 184 (M184L, M184V, M184I and M184A), which were designed to affect the enzyme specificity by changing the hydrophobic channel that gives access to the active center, exhibited an increase in activity following a longer incubation period.

TABLE 9

| Mutation | 4 hours at 37° C. | | 20 hours at 37° C. | |
| --- | --- | --- | --- | --- |
| | Average Ambroxan peak area % | Average difference (% peak area) * | Average Ambroxan peak area % | Average difference (% peak area) * |
| V45L + T326S | 48.5 | +11 | 68 | +20.5 |
| G623A | 36 | −1.5 | 74.5 | +27 |
| F624Y | 55 | +17.5 | 68.5 | +21 |
| F624A | 33.5 | −4 | 54.5 | +7 |
| F460A | 26.5 | −11 | 60.5 | +13 |
| E46Q | 45.5 | +8 | 82.5 | +35 |
| M184L | 40 | +2.5 | 68 | +20.5 |
| M184V | 40.5 | +3 | 69 | +21.5 |
| M184I | 47.5 | +10 | 80.5 | +33 |
| M184A | 34 | −3.5 | 66 | +18.5 |
| R194Q | 33.5 | −4 | 59 | +11.5 |
| Y658F | 29 | −8.5 | 51 | +3.5 |
| Q178E | 48 | +10.5 | 67.5 | +20 |
| E46H | 32.5 | −5 | 55.5 | +8 |
| Q54E | 27.5 | −10 | 66 | +18.5 |
| Wild-type | 37.5 | 0 | 47.5 | 0 |

* Average difference in ambroxan production vs SHC wild-type.

In addition to ambroxan, mutants were also tested for sclareolide production from homofarnesic acid. This analysis indicated that the G623V, I278V, L335F and Q54E mutants exhibited an increase in sclareolide production compared to wild-type GmSHC (Table 10).

TABLE 10

| Mutation | Average increase in sclareolide production vs SHC WT (% peak area) |
| --- | --- |
| L656E | +0.2 |
| V45I | +0.3 |
| V45Q | +0.2 |
| G623A | +0.2 |
| G623V | +1.6 |
| I278V | +1.7 |
| E386Q | +0.2 |
| L335F | +1.6 |
| Q178E | +1 |
| E46H | +1 |
| Q54E | +1.4 |

FIG. 2 shows that after the 4-hour incubation only seven mutants demonstrated higher ambroxan production than the wild-type SHC (bars all above the dashed line), whereas 15 mutants exhibited higher activity following the 20-hour incubation (FIG. 2). In particular, the V45L+T326S, F624Y, E46Q, M184L, M184V, M184I and Q178E mutants demonstrated increased activity at both time points. In addition to these seven mutants, in silico and in vitro analyses indicated that the G623A, Q54E, R194Q and M184A mutants were also of interest. Accordingly, combination mutants are provided, which exhibit additive or synergistic effects to increase the activity of the GmSHC enzyme (Table 11).

TABLE 11

| Conjugated Mutants | | |
| --- | --- | --- |
| E46Q + M184I | E46Q + M184A | E46Q + M184V |
| E46Q + M184I + | E46Q + M184I + | E46Q + M184I + |
| G623A | F624Y + G623A + V45L + T326S | F624Y + G623A |
| M184I + Q178E | E46Q + F624Y | Q54E + M184I |
| M184V + Q178E | E46Q + G623A | E46Q + M184I + F624Y |
| E46Q + M184I + F624Y + R194Q + V45L + T326S + G623A | E46Q + M184I + R194Q | E46Q + M184I + V45L + T326S |
| E46Q + M184I + F624Y + R194Q | E46Q + M184I + F624Y + R194Q + V45L + T326S | E46Q + M184L |
| Q54E + R194Q | Q54E + E46Q | Q54E + M184I + F624Y |
| Q54E + M184I + V45L + T326S | Q54E + M184I + F624Y + T326S | Q54E + E46Q + M184I + F624Y |
| Q54E + R194Q + V45L + T326S | Q54E + E46Q + M184I + V45L + T326S | Q54E + M184I + V45L + T326S + F624Y |

Figure 3:
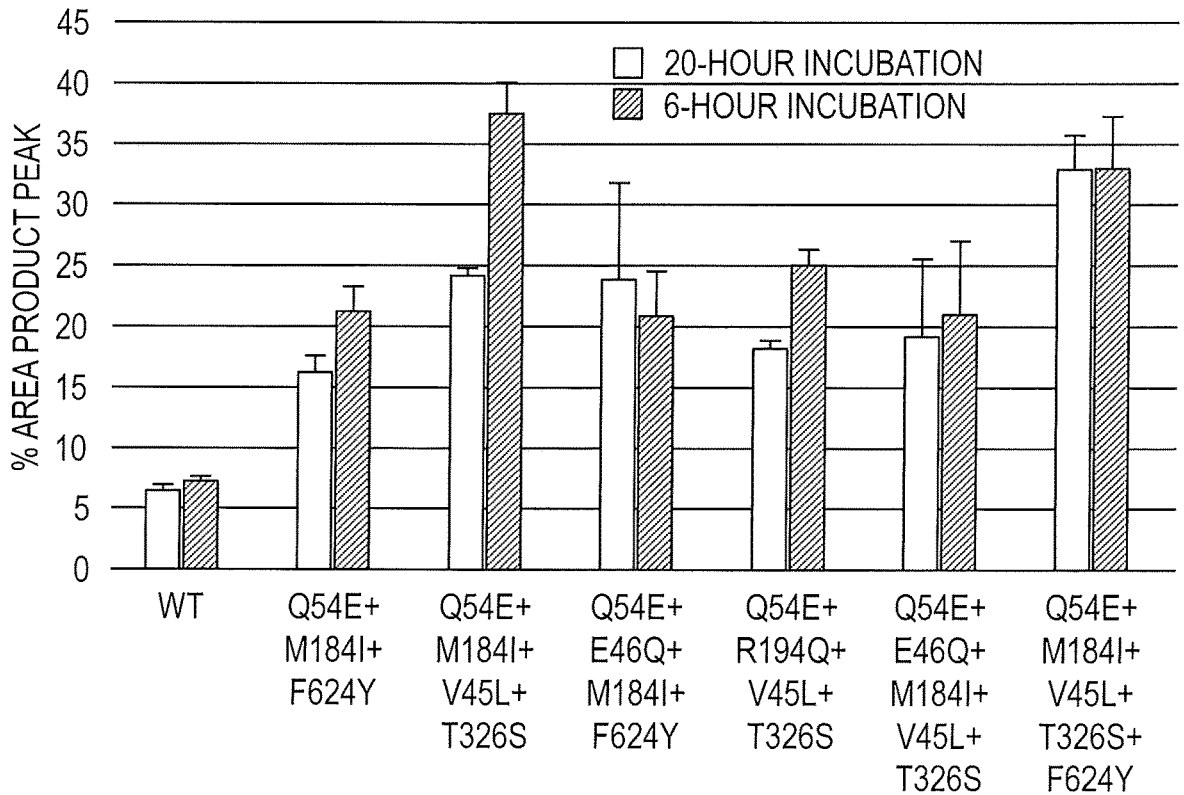
FIG. 3 shows the % area ambroxan product peak by mutant GmSHC enzymes following incubation at 37° C. for 6 and 20 hours with 50 mg/mL homofarnesol at 25% enzyme loading.

When selected combination mutants were incubated with 50 mg/mL homofarnesol for 20 hours, it was found that each of the mutants exhibited an increase in activity compared to wild-type GmSHC (Table 12). Similar results were observed when the combination mutants were incubated with 50 mg/mL homofarnesol for 6 or 20 hours at 25% enzyme loading (FIG. 3).

TABLE 12

| Mutation | % Area Ambroxan Product Peak |
| --- | --- |
| Wild-type | 18.25 |
| E46Q + M184I + V45L + T326S | 21.20 |
| Q54E + M184I | 21.86 |
| Q54E + R194Q | 21.39 |
| Q54E + E46Q | 20.02 |
| Q54E + M184I + F624Y | 35.10 |
| Q54E + M184I + V45L + T326S | 28.96 |
| Q54E + M184I + F624Y + T326S | 21.57 |

Example 6: Summary of GmSHC Derivatives

SHCs are integral monotopic membrane proteins that adopt a dimeric 3D arrangement. Each monomer is characterized by QW motifs that tightly connect numerous α-helices building up two highly stable α/α-barrels domains (Wendt et al. (1999) *J. Mol. Biol.* 286:175-87). The active center cavity is buried within the two α/α-barrels domains and its access is possible through an inner hydrophobic channel, which it is suggested to be the membrane-immersed region of the enzyme (Lenhart, et al. (2002) *Chem. Biol.* 9:639-45). The channel and the active center cavity are separated by a narrow constriction which is responsible for substrate recognition (Lenhart, et al. (2002) *Chem. Biol.* 9:639-45). For GmSHC, those residues correspond to Phe176, Met184, Phe457 and Cys458. The residues that constitute the conserved DXDD motif (Wendt et al. (1999) *J. Mol. Biol.* 286:175-87), are found at the top of the activity center cavity. One of those residues is Asp396, the first proton donor, which initiates cyclization of homofarnesol by donating a proton to the double bond C2=C3. The DXDD motif is followed by tryptophan, tyrosine and phenylalanine residues that are responsible for stabilizing the cationic intermediates by strong cation-n interactions (Dougherty (1996) *Science* 271:163-8). On the bottom of the cavity is a negatively charged residue, the last proton acceptor, which receives a proton from the hydroxyl group thereby resulting in closure of the third ring and formation of ambroxan.

To improve the conversion of homofarnesol to ambroxan, GmSHC was mutated at one or more of the residues at position 45, 46, 54, 178, 184, 194, 247, 278, position 326, 386, 335, 460, 623 and 624 of SEQ ID NO:2.

Positions 45 and 326.

According to the GmSHC homology model and molecular docking calculations, residues V45 and T326 are placed near the substrate hydroxyl group. GmSHC position 45 is mutated to glutamine, leucine or isoleucine and position 326 to serine in order to increase the intermolecular interactions with the substrate. The combination of both these mutations (V45L+T326S) showed a 1.4-fold increase in ambroxan production after a 20-hour incubation with 15 g/L homofarnesol.

Positions 46, 54 and 386.

According to GmSHC homology model and molecular docking calculations, residues E46 or E386 function as a last proton acceptor, receiving a proton from the substrate hydroxyl group. A structural alignment between AaSHC (Reinhert, et al. (2004) Chem. Biol. 11:121-6) and the GmSHC homology model indicates that Q54 of GmSHC is superimposed with residue E45 of AaSHC, which is the last proton acceptor of this enzyme (Dang & Prestwich (2000) Chem. Biol. 7:643-9). Therefore, residue 54 of GmSHC was mutated to glutamate to incorporate a last proton acceptor at this position, without having a negative impact on the charge network associated with the conserved DXDD motif. Residue 46 was mutated to glutamine, alanine or histidine, while residue 386 was mutated to glutamine to change the last proton acceptor position. When compared to the wild-type enzyme, mutants with mutations at position E386 had no effect on enzyme activity. However, mutations at positions E46 and Q54 both showed an increase in conversion of homofarnesol to ambroxan. After a 20-hour incubation of 15 g/L homofarnesol, the E46Q and E46H mutants respectively exhibited a 1.8-fold and 1.2-fold improvement in activity, whereas the Q54E mutant exhibited a 1.4-fold improvement in activity compared to the wild-type enzyme.

Position 178.

A structural alignment between the GmSHC homology model and the homologous human lanosterol synthase (Thoma, et al. (2004) Nature 432:118-22) indicates that Q178 of GmSHC is superimposed with residue H232 of the human lanosterol synthase, which is the last proton acceptor of this enzyme. Therefore, residue 178 of GmSHC was mutated to glutamate to incorporate a last proton acceptor at this position. The introduction of this mutation increased conversion of homofarnesol to ambroxan by 1.4-fold compared to the wild-type enzyme.

Position 184.

Residue M184 is placed in narrow constriction, which is responsible for substrate recognition (Lenhart, et al. (2002) Chem. Biol. 9:639-45). Thus, to alter the substrate recognition, M184 of GmSHC was mutated to non-polar amino acids, i.e., Leucine, Isoleucine, Valine and Alanine. By mutating this position, any methionine oxidation phenomenon is also prevented, which could negatively affect substrate recognition. It was observed that mutation of M184 to any one of Leu, Ile, Val or Ala resulted in an increase in activity. Notably, the M184I mutant exhibited the largest increase, with a 1.7-fold improvement in conversion of homofarnesol to ambroxan.

Position 194.

QW motifs firmly connect the α-helices contributing to the build-up of two α/α-barrels. These highly stable α/α-barrels protect the enzyme against the energy release associated with the highly exergonic catalyzed reaction. According to the homology model of GmSHC, residue R194 is placed near residue W152. Therefore, residue 194 was mutated to glutamine in order to introduce a new QW motif with W152, thereby increasing the structural stability of the enzyme. Experimentally, this mutation showed improvements in conversion with a 1.3-fold improvement in conversion of homofarnesol to ambroxan.

Position 247.

According to the GmSHC homology model, residue P247 is placed in a loop at the channel entrance, which is suggested to be the membrane-immersed region of the enzyme. Residue P247 was mutated to a non-proline residue to change the dynamics of the channel in this region. When tested in the combination mutant, V45L+T326S+M184I+R194Q, a 2.7-fold improvement in conversion was observed when incubated with 50 g/L homofarnesol at 40% enzyme loading.

Position 278. According to the GmSHC homology model and the molecular docking calculations, residue I278 is placed right below the substrate hydroxyl group. When residue I278 is mutated to valine, the molecular docking calculations indicate that the substrate arrangement within the active center improves by placing the substrate C2=C3 double bond closer to D396, the first proton donor. Mutation of residue I278 did not show any improvements in homofarnesol conversion; however when the enzyme was incubated with homofarnesic acid, the conversion of acid to sclareolide showed a 2-fold improvement when compared to the wild type enzyme when tested at 10 g/L substrate loading and 100% enzyme loading.

Position 335.

According to the GmSHC homology model and the molecular docking calculations, residue L335 is placed near residue D396, the first proton donor, and when mutated to phenylalanine it can introduce a strong cation-n interaction with the substrate cationic intermediate. Mutations at this position provided a 1.8-fold improvement with regards to the conversion of homofarnesic acid to sclareolide.

Position 460.

According to the GmSHC homology model, residue F460 of GmSHC is a residue in the active center cavity next to the narrow constriction that is responsible for substrate recognition (Lenhart, et al. (2002) Chem. Biol. 9:639-45). Residue F460 was mutated to alanine to increase the access of the substrate to the active center cavity. As a result, this mutation showed a 1.3-fold improvement when reacted with homofarnesol at 15 g/L substrate loading.

Position 623.

According to the GmSHC homology model and the molecular docking calculations, residue G623 is positioned closed to hydroxyl group of the substrate. Accordingly, residue G623 was mutated to alanine or valine to increase the intermolecular interactions with the substrate. While the G623A mutant showed a 1.6-fold improvement in ambroxan production in the presence of 15 g/L homofarnesol, the G623V mutant exhibited a 1.9-fold increase in the conversion of homofarnesic acid to sclareolide.

Position 624.

According to the GmSHC homology model and the molecular docking calculations, residue F624 establishes a strong cation-n interaction, stabilizing the cationic intermediate. Therefore, residue F624 was mutated to tyrosine or tryptophan to introduce an even stronger cation-n interaction with the substrate cationic intermediate. When this position was altered to tryptophan, a 1.45-fold improvement in the production of ambroxan from homofarnesol was obtained.

What is claimed is:

1. A recombinant vector comprising a nucleic acid molecule encoding Squalene Hopene Cyclase (SHC), wherein the amino acid sequence is (i) SEQ ID NO: 2 or (ii) an amino acid sequence having at least 90% sequence identity with SEQ ID NO: 2, and the SHC of (i) or (ii) comprises an amino acid substitution, relative to SEQ ID NO:2, at position 45, 46, 54, 86, 139, 142, 178, 184, 194, 239, 278, 326, 335, 386, 455, 460, 603, 623, 624, 656, 658 or a combination thereof and wherein the SHC produces ambroxan a fragrance ingredient.

2. A recombinant host cell comprising the recombinant vector of claim 1.

3. A method for producing ambroxan comprising
   (a) providing homofarnesol to a recombinant host cell that expresses Squalene Hopene Cyclase (SHC), wherein the amino acid sequence is (i) SEQ ID NO:2 or (ii) an amino acid sequence having at least 90% sequence identity with SEQ ID NO:2, and the SHC of (i) or (ii) comprises an amino acid substitution, relative to SEQ ID NO:2, at position 45, 46, 54, 86,139,142,178, 184, 194, 239, 278, 326, 335, 386, 455, 460, 603, 623, 624, 656, 658 or a combination thereof, and
   (b) collecting ambroxan produced by the SHC, and wherein the ambroxan is a fragrance ingredient.

4. The method of claim 3, wherein the homofarnesol is provided in the presence of a solubilizing agent.

5. The method of claim 4, wherein the solubilizing agent comprises a nonionic surfactant.

6. The method of claim 3, wherein the homofarnesol comprises (3E,7E) homofarnesol.

* * * * *